United States Patent
Fishman et al.

(10) Patent No.: US 11,407,872 B2
(45) Date of Patent: Aug. 9, 2022

(54) FOAM COMPOSITIONS COMPRISING POLYLACTIC ACID POLYMER, POLYVINYL ACETATE POLYMER AND PLASTICIZER, ARTICLES, AND METHODS OF MAKING AND USING SAME

(71) Applicant: 3M INNOVATIVE PROPERTIES COMPANY, St. Paul, MN (US)

(72) Inventors: Joshua M. Fishman, Minneapolis, MN (US); Caitlin E. Meree, St. Paul, MN (US); Ning Zhou, Vadnais Heights, MN (US); Derek J. Dehn, Maplewood, MN (US); Jacob D. Young, St. Paul, MN (US); Jeffrey O. Emslander, City of Grant, MN (US); Bradley L. Givot, St. Paul, MN (US); Aaron T. Hedegaard, Woodbury, MN (US); Justin M. Bolton, Minneapolis, MN (US); Terry R. Hobbs, Stillwater, MN (US); Mahfuza B. Ali, Mendota Heights, MN (US); Robert C. Coffin, Zionsville, MN (US); Brant U. Kolb, Afton, MN (US); Paul D. Pennington, Farmington, MN (US); Jimmie R. Baran, Jr., Prescott, WI (US); Duane D. Fansler, Dresser, WI (US); Ying Lin, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 44 days.

(21) Appl. No.: 16/308,642

(22) PCT Filed: Jun. 14, 2017

(86) PCT No.: PCT/US2017/037460
§ 371 (c)(1),
(2) Date: Dec. 10, 2018

(87) PCT Pub. No.: WO2017/222891
PCT Pub. Date: Dec. 28, 2017

(65) Prior Publication Data
US 2019/0256677 A1 Aug. 22, 2019

Related U.S. Application Data

(60) Provisional application No. 62/352,633, filed on Jun. 21, 2016.

(51) Int. Cl.
C08L 29/14 (2006.01)
C08J 9/00 (2006.01)
A61F 11/08 (2006.01)
A61F 11/14 (2006.01)
C08J 5/18 (2006.01)
(Continued)

(52) U.S. Cl.
CPC .............. *C08J 9/0061* (2013.01); *A61F 2/08* (2013.01); *A61F 2/14* (2013.01); *A61F 11/08* (2013.01); *A61F 11/14* (2013.01); *C08J 5/18* (2013.01); *C08J 9/0071* (2013.01); *C08J 9/102* (2013.01); *C08J 9/103* (2013.01); *C08J 9/32* (2013.01); *C08L 29/14* (2013.01); *C08L 67/04* (2013.01); *G10K 11/16* (2013.01); *C08J 9/009* (2013.01); *C08J 9/0023* (2013.01); *C08J 9/0028* (2013.01); *C08J 9/0038* (2013.01); *C08J 9/0052* (2013.01); *C08J 9/122* (2013.01); *C08J 2201/026* (2013.01); *C08J 2203/04* (2013.01); *C08J 2203/06* (2013.01); *C08J 2205/052* (2013.01); *C08J 2329/14* (2013.01); *C08J 2331/04* (2013.01); *C08J 2367/04* (2013.01); *C08J 2429/14* (2013.01); *C08J 2431/04* (2013.01); *C08J 2467/04* (2013.01); *C08J 2471/02* (2013.01); *C08L 2203/14* (2013.01); *C08L 2205/03* (2013.01); *C08L 2205/06* (2013.01);
(Continued)

(58) Field of Classification Search
CPC .. C08L 67/04; C08L 2203/14; C08L 2312/00; C08F 118/08
See application file for complete search history.

(56) References Cited

U.S. PATENT DOCUMENTS

| | | |
|---|---|---|
| 4,766,182 A | 8/1988 | Murdoch |
| 5,210,108 A | 5/1993 | Spinu |

(Continued)

FOREIGN PATENT DOCUMENTS

| | | |
|---|---|---|
| CN | 1061421 | 5/1992 |
| CN | 1786072 | 6/2006 |

(Continued)

OTHER PUBLICATIONS

Lai et al Preparation and Properties of Melt-Blended Polylactic Acid/ Polyethylene Glycol-Modified Silica Nanocomposites, Journal of Applied Polymer Science, 2013, pp. 496-503, published online Mar. 19, 2013.*

(Continued)

*Primary Examiner* — Gregory Listvoyb
(74) *Attorney, Agent, or Firm* — Adrian L. Pishko

(57) ABSTRACT

Foam compositions are provided including a polylactic acid polymer; second (e.g., polyvinyl acetate) polymer having a glass transition temperature ($T_g$) of at least 25° C.; and plasticizer. Also described are articles comprising the foam compositions, such as a sheet or hearing protection article. Methods of making and using the foam compositions are further described herein.

11 Claims, 11 Drawing Sheets

(51) Int. Cl.
*C08J 9/10* (2006.01)
*C08L 67/04* (2006.01)
*G10K 11/16* (2006.01)
*A61F 2/14* (2006.01)
*C08J 9/32* (2006.01)
*A61F 2/08* (2006.01)
*C08J 9/12* (2006.01)

(52) U.S. Cl.
CPC ....... *C08L 2205/24* (2013.01); *C08L 2312/00* (2013.01)

(56) References Cited

U.S. PATENT DOCUMENTS

| | | | |
|---|---|---|---|
| 5,238,968 A * | 8/1993 | Morita | B29C 44/5627 |
| | | | 521/182 |
| 5,773,497 A * | 6/1998 | Ueyanagi | C08K 5/3435 |
| | | | 524/99 |
| 5,866,053 A | 2/1999 | Park | |
| 6,005,068 A | 12/1999 | Gruber | |
| 6,586,483 B2 | 7/2003 | Kolb | |
| 7,033,975 B2 | 4/2006 | Baran, Jr | |
| 8,080,194 B2 | 12/2011 | Nadella | |
| 8,729,171 B2 | 5/2014 | Kannan | |
| 9,145,478 B2 | 9/2015 | Costeux | |
| 2010/0062235 A1 | 3/2010 | Nadella | |
| 2010/0087556 A1* | 4/2010 | Britton | C08J 9/0061 |
| | | | 428/407 |
| 2010/0199884 A1 | 8/2010 | Bastos | |
| 2012/0053256 A1 | 3/2012 | Chen | |
| 2012/0196958 A1 | 8/2012 | Park | |
| 2012/0321873 A1 | 12/2012 | Costeux | |
| 2014/0116702 A1* | 5/2014 | Tang | C09K 8/68 |
| | | | 166/295 |
| 2014/0221512 A1 | 8/2014 | Costeux | |
| 2015/0283285 A1 | 10/2015 | Karls | |

FOREIGN PATENT DOCUMENTS

| | | |
|---|---|---|
| CN | 101481503 | 7/2009 |
| CN | 101362833 | 8/2012 |
| CN | 102718983 | 10/2012 |
| CN | 102796277 | 4/2014 |
| EP | 1449869 | 8/2004 |
| EP | 1735373 | 2/2012 |
| EP | 2792704 | 10/2014 |
| JP | 2005-206813 | 8/2005 |
| JP | 2010-077180 | 4/2010 |
| JP | 2006-022242 | * 10/2010 |
| WO | WO 90-01521 | 2/1990 |
| WO | WO 92/04413 | 3/1992 |
| WO | WO 2010-052019 | 5/2010 |
| WO | WO 2011-058014 | 5/2011 |
| WO | WO 2011-082052 | 7/2011 |
| WO | WO 2013-030300 | 3/2013 |
| WO | WO 2014-001119 | 1/2014 |
| WO | WO 2014-158014 | 10/2014 |
| WO | WO 2014-210523 | 12/2014 |
| WO | WO 2015-052019 | 4/2015 |
| WO | WO 2015-065557 | 5/2015 |
| WO | WO 2016-105998 | 6/2016 |
| WO | WO 2017-105887 | 6/2017 |
| WO | WO 2017-112386 | 6/2017 |
| WO | WO 2017-142730 | 8/2017 |
| WO | WO 2017-222863 | 12/2017 |

OTHER PUBLICATIONS

Costeaux, "$CO_2$-Blown Nanocellular Foams", Journal of Applied Polymer Science, 2014, pp. 41293, 16 pages.

Jia, "Foaming and Damping Properties of Ethylene Vinyl-Acetate Copolymer/Polylactic Acid Blends", Journal of Macromolecular Science, Part B: Physics, 2015, vol. 54, pp. 190-202.

Liu, "Improving Melt Strength of Polylactic Acid", Intern. Polymer Processing XXVIII, 2013, pp. 64-71.

Matuana, "Solid state microcellular foamed poly(lactic acid): Morphology and property characterization", Bioresource Technology, 2008, vol. 99, pp. 3643-3650.

Mosanenzadeh, "Development of Polylactide Open-Cell Foams with Bimodal Structure for High Acoustic Absorption", Journal of Applied Polymer Science, 2013, vol. 131, pp. 39518, 11 pages.

Mosanenzadeh, "Development, Characterization, and Modeling of Environmentally Friendly Open-Cell Acoustic Foams", Polymer Engineering and Science, 2013, pp. 1979-1989.

Mosanenzadeh, "Effect of Biopolymer Blends on Physical and Acoustical Properties of Biocomposite Foams", Journal of Polymer Science, Part—B: Polymer Physics, 2014, vol. 52, No. 15, pp. 1002-1013.

Okamoto, "A Slow Shape-Recovery Polymer Based on Polylactic Acid", Journal of Applied Polymer Science, 2014, vol., pp. 41004, 4 pages.

International Search report for PCT International application No. PCT/US2017/037460 dated Oct. 30, 2017, pp. 6.

* cited by examiner

500μm

500μm

500μm

500μm

500μm

500μm

FOAM COMPOSITIONS COMPRISING POLYLACTIC ACID POLYMER, POLYVINYL ACETATE POLYMER AND PLASTICIZER, ARTICLES, AND METHODS OF MAKING AND USING SAME

CROSS REFERENCE TO RELATED APPLICATIONS

This application is a national stage filing under 35 U.S.C. 371 of PCT/US2017/037460, filed Jun. 14, 2017, which claims the benefit of U.S. Application No. 62/352,633, filed Jun. 21, 2016, the disclosures of which are incorporated by reference in their entireties herein.

FIELD

The present disclosure relates to foam compositions including polylactic acid polymers, articles, and methods of forming and using the foam compositions.

BACKGROUND

Foams formed from polyvinyl chloride (PVC) have been used in industry; however, PVC is difficult to recycle and thus foams made of a more sustainable material would be advantageous.

SUMMARY

In a first aspect, a foam composition is provided. The foam composition includes a polylactic acid polymer; a second (e.g., polyvinyl acetate) polymer having a $T_g$ of at least 25° C.; and a plasticizer. The foam composition comprises a closed cell foam.

In a second aspect, another foam composition is provided. The foam composition includes a polylactic acid polymer; a second (e.g., polyvinyl acetate) polymer having a $T_g$ of at least 25° C.; and a plasticizer. The foam composition comprises an open celled foam.

In a third aspect, a foam sheet is provided. The foam sheet includes the foam composition according to the first aspect or the second aspect.

In a fourth aspect, a method of making a foam composition is provided. The method includes compressing a mixture comprising a polylactic acid polymer; a second (e.g., polyvinyl acetate) polymer having a $T_g$ of at least 25° C.; a plasticizer; and a blowing agent; and heating the compressed mixture, thereby forming the foam composition.

In a fifth aspect, another method of making a foam composition is provided. The method includes subjecting a mixture to an elevated pressure; and diffusing a gas into the mixture, followed by ending the subjection to the elevated pressure, thereby forming the foam composition. The mixture includes a polylactic acid polymer; a second (e.g., polyvinyl acetate) polymer having a $T_g$ of at least 25° C.; and a plasticizer.

In a sixth aspect, a hearing protection article is provided. The hearing protection article includes the foam composition according to the first aspect or the second aspect.

In a seventh aspect, a process is provided. The process includes providing at least one hearing protection article according to the fourth aspect; and interposing the hearing protection article between an acoustic source and an acoustic receiver in the form of a human ear.

DETAILED DESCRIPTION

Figure 1A:
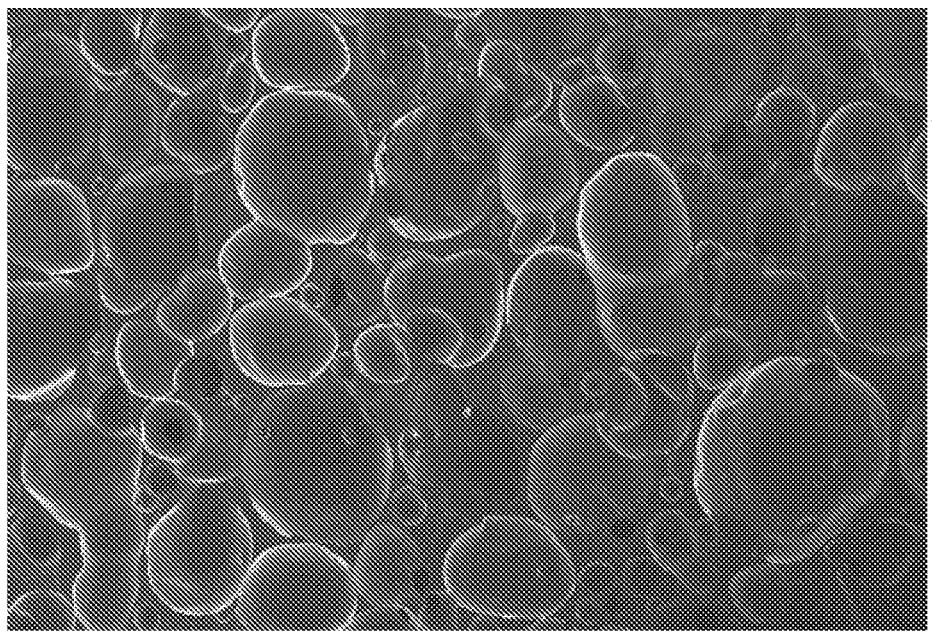
FIG. 1A is a scanning electron microscope (SEM) image of the foam composition of Example 14.
Figure 1B:
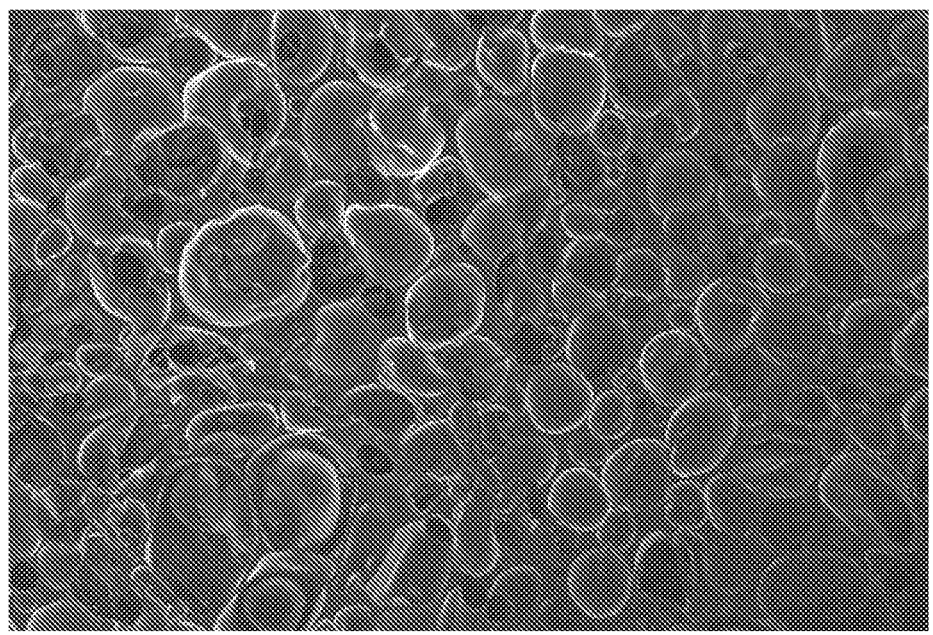
FIG. 1B is an SEM image of the foam composition of Example 15.
Figure 1C:
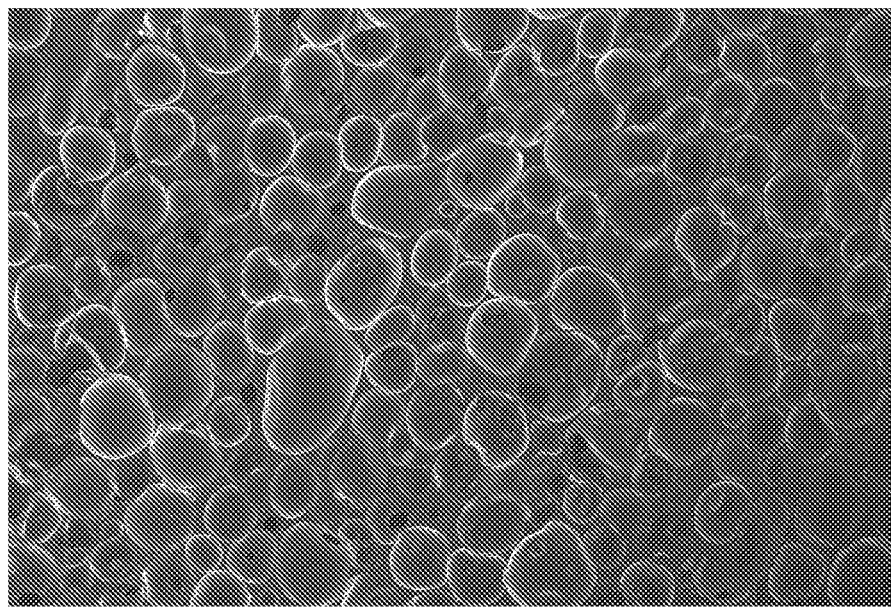
FIG. 1C is an SEM image of the foam composition of Example 21.
Figure 2A:
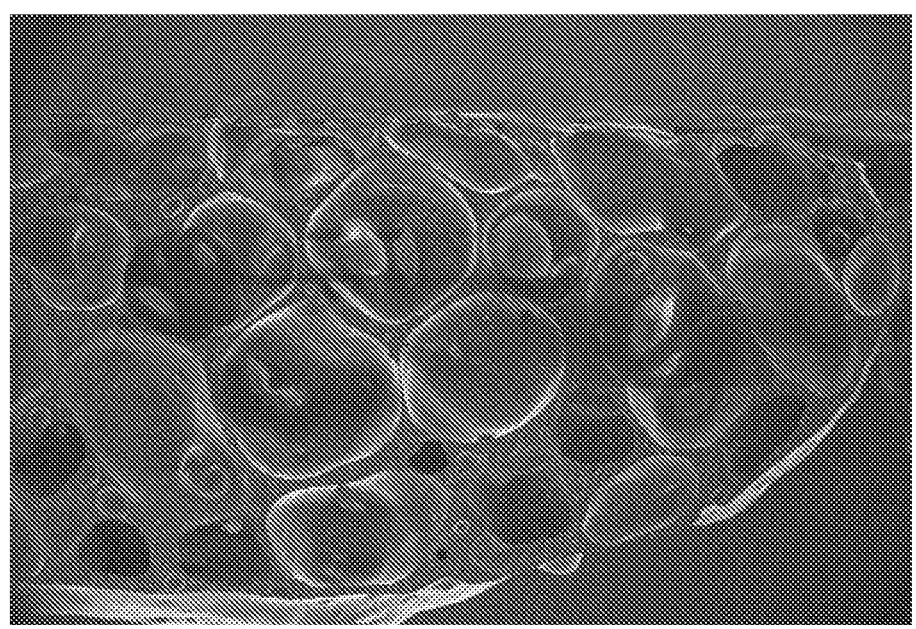
FIG. 2A is an SEM image of the foam composition of Example 26.
Figure 2B:
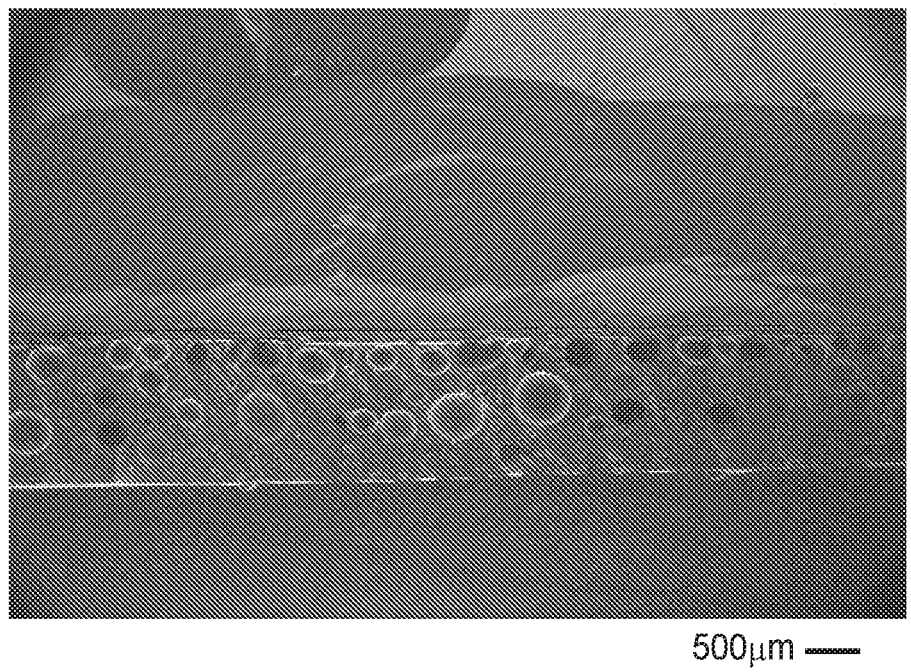
FIG. 2B is an SEM image of the foam composition of Example 27.
Figure 3A:
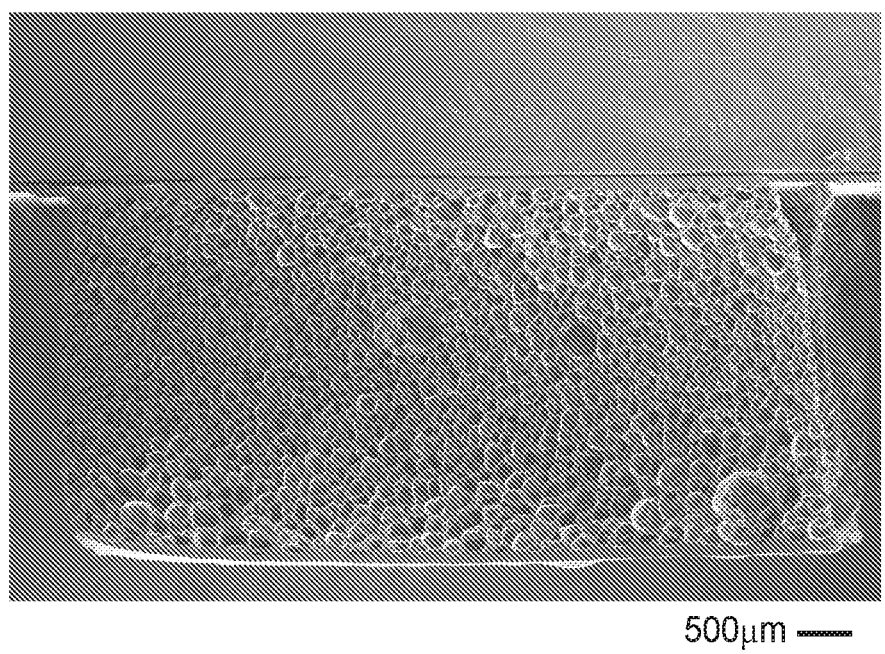
FIG. 3A is an SEM image of the foam composition of Example 28.
Figure 3B:
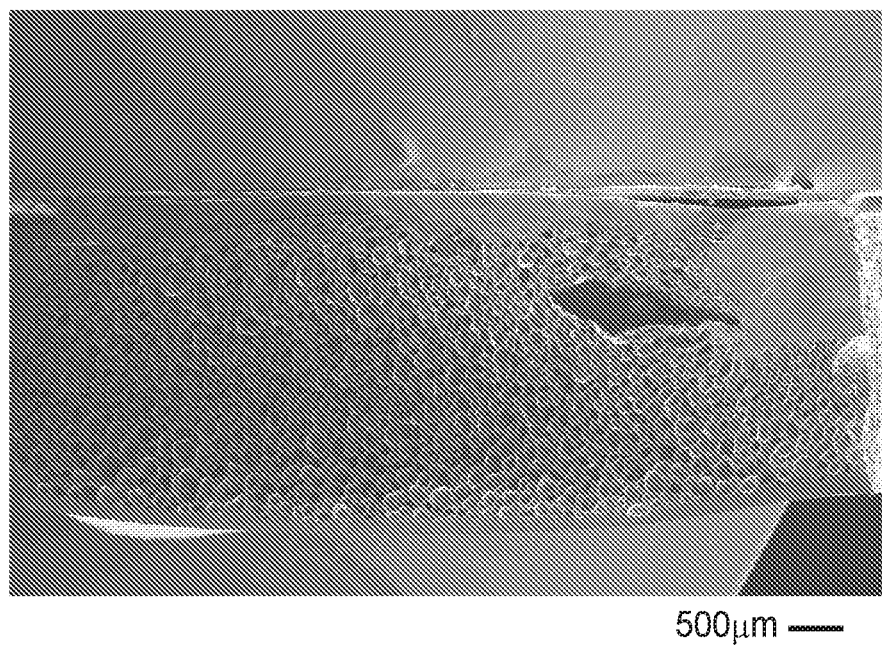
FIG. 3B is an SEM image of the foam composition of Example 29.
Figure 3C:
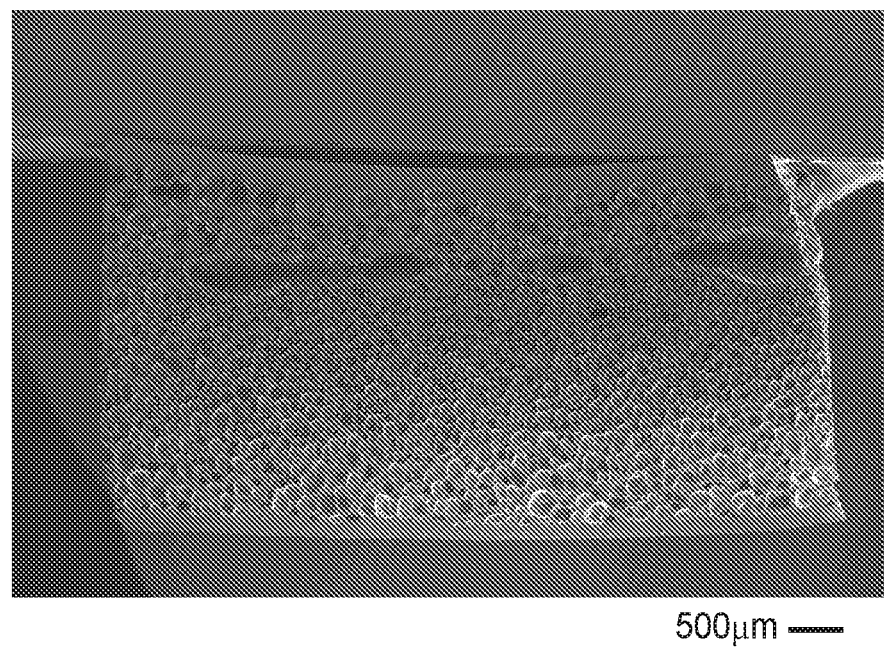
FIG. 3C is an SEM image of the foam composition of Example 30.
Figure 3D:
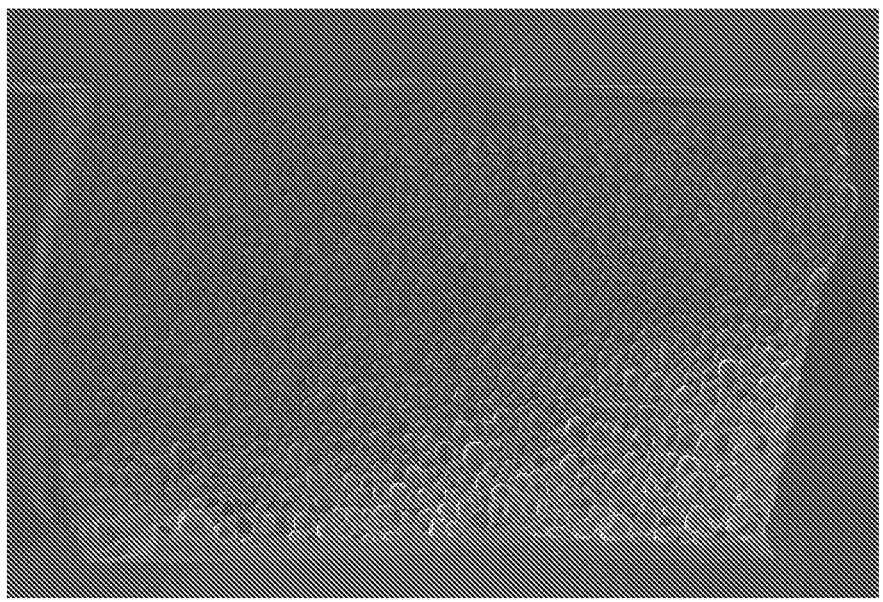
FIG. 3D is an SEM image of the foam composition of Example 31.
Figure 3E:
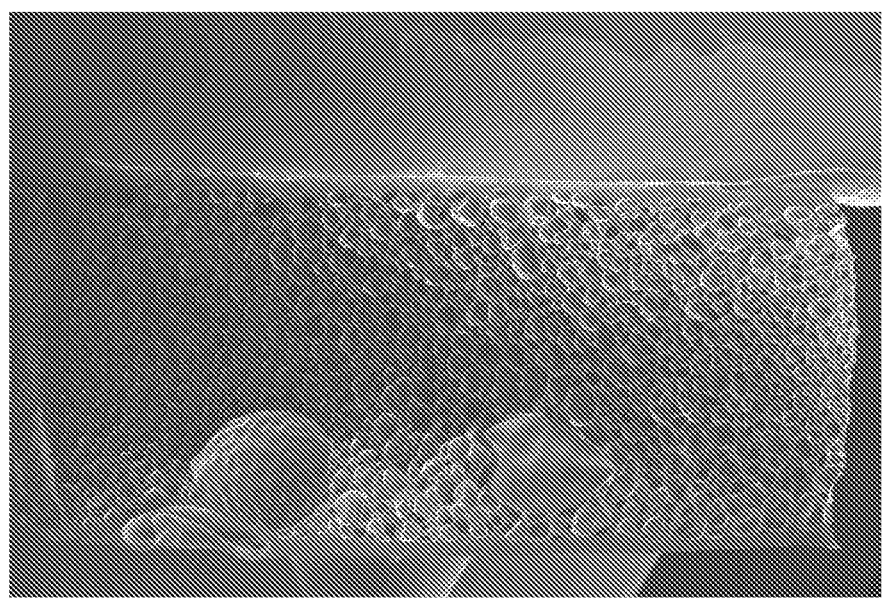
FIG. 3E is an SEM image of the foam composition of Example 32.
Figure 3F:
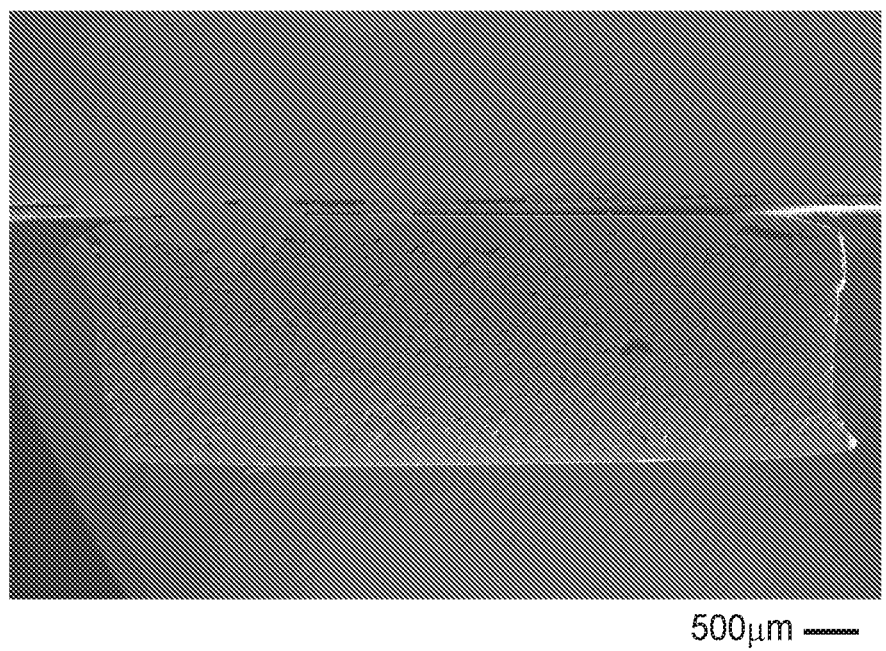
FIG. 3F is an SEM image of the foam composition of Example 38.
Figure 4A:
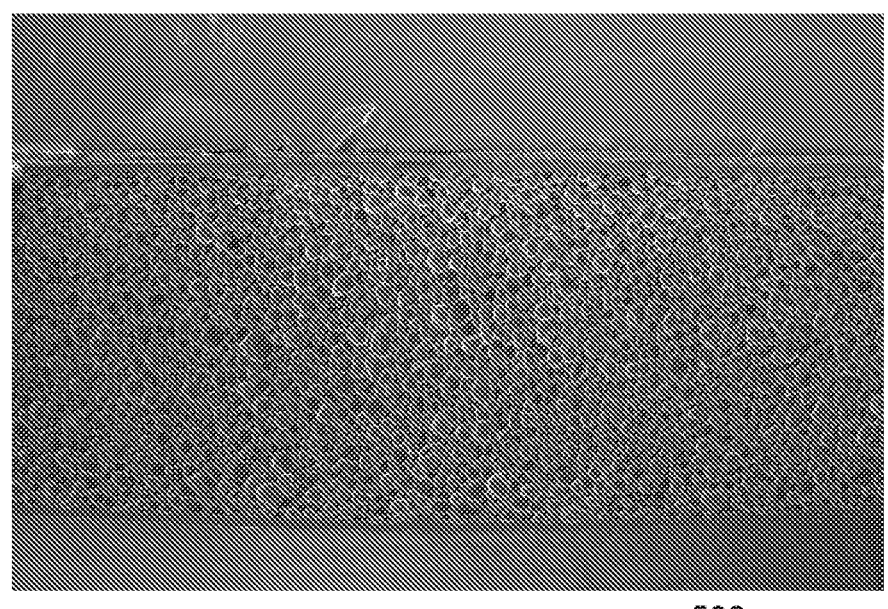
FIG. 4A is an SEM image of the foam composition of Example 33.
Figure 4B:
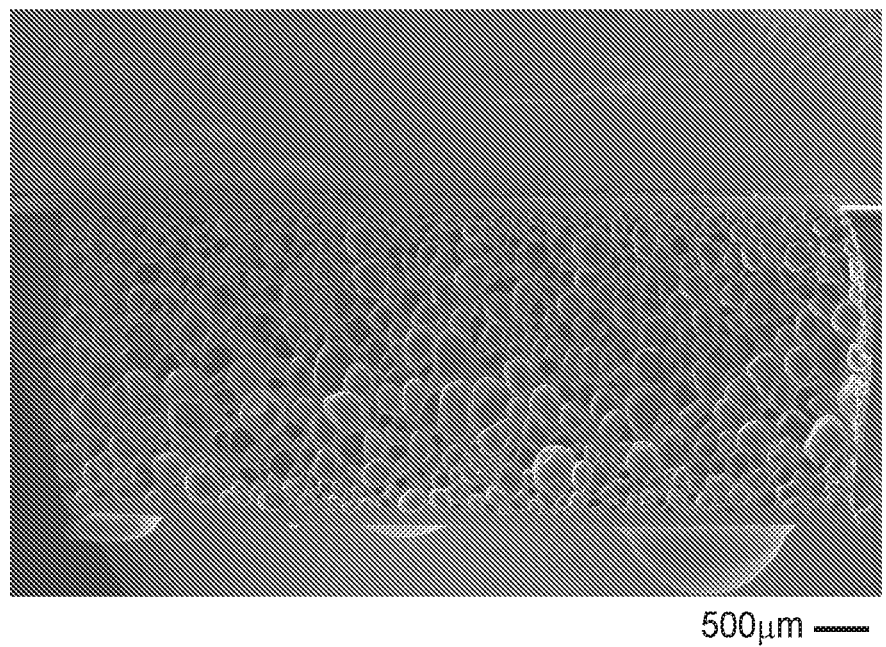
FIG. 4B is an SEM image of the foam composition of Example 34.
Figure 4C:
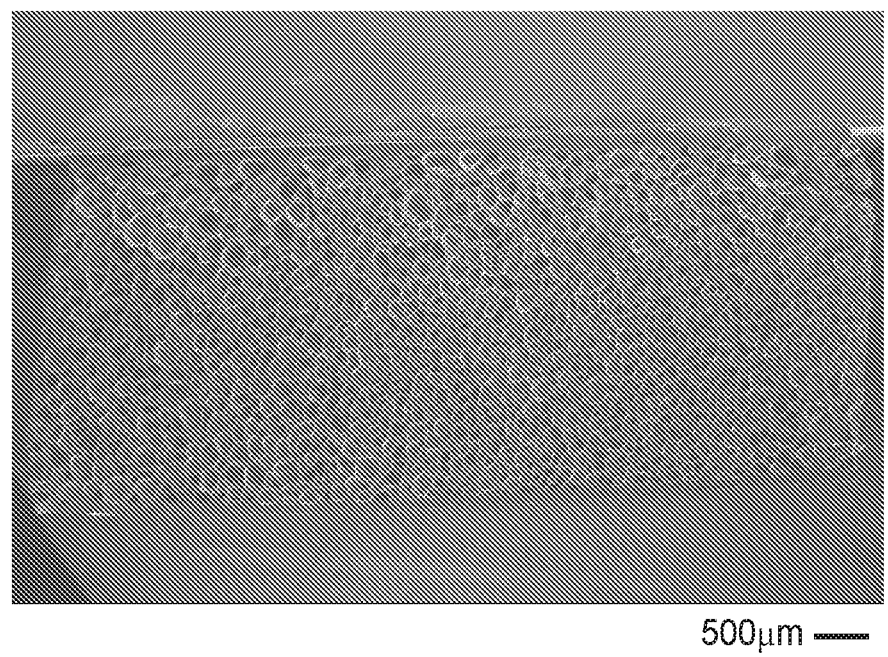
FIG. 4C is an SEM image of the foam composition of Example 33.
Figure 4D:
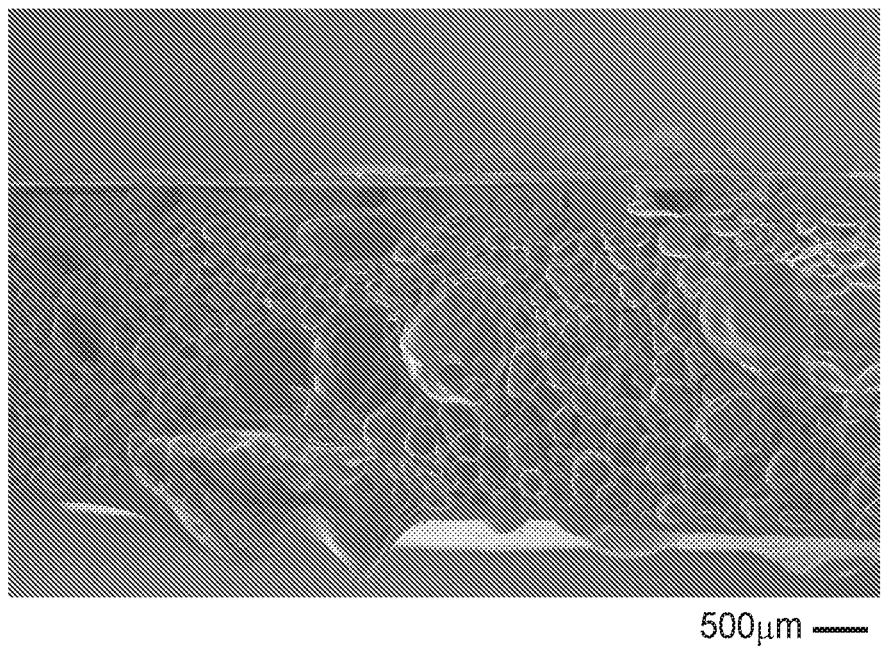
FIG. 4D is an SEM image of the foam composition of Example 36.
Figure 4E:
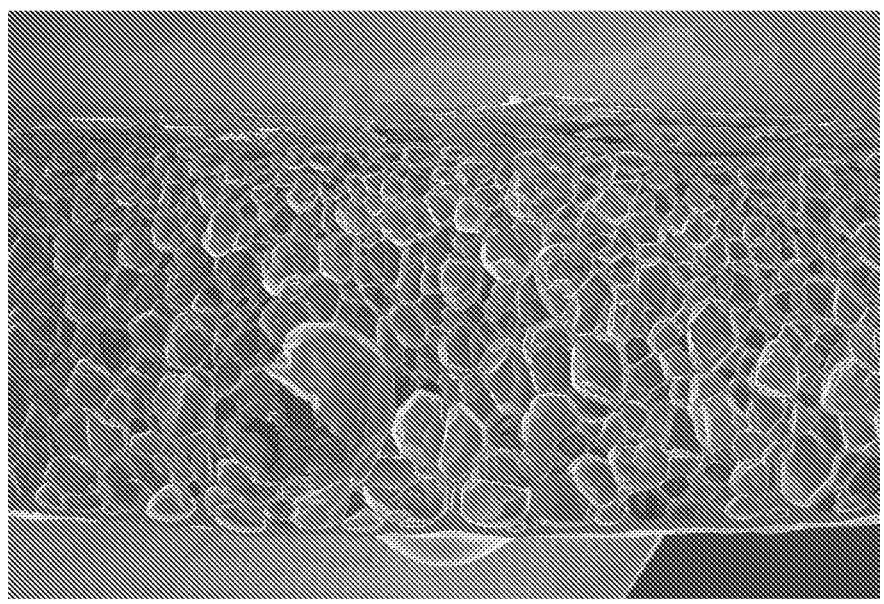
FIG. 4E is an SEM image of the foam composition of Example 37.

In a first aspect, a foam composition is provided. The foam composition comprises a polylactic acid polymer; a second (e.g., polyvinyl acetate) polymer having a $T_g$ of at least 25° C.; and a plasticizer. The foam composition comprises a closed cell foam, which means that the foam contains substantially no connected cell pathways that extend from one outer surface through the material to another outer surface. A closed cell foam can include up to about 10% open cells, within the meaning of "substantially" no connected cell pathways.

In a second aspect, another foam composition is provided. The foam composition comprises a polylactic acid polymer; a second (e.g., polyvinyl acetate) polymer having a $T_g$ of at least 25° C.; and a plasticizer. The foam composition comprises an open celled foam, which means that the majority of the cells (voids) are interconnected rather than being isolated as in a closed-cell foam. An open celled foam can include up to about 10% closed cells.

The foam compositions described herein comprise polylactic acid ("PLA") polymer. Lactic acid is a renewable material obtained by the bacterial fermentation of corn starch or cane sugar, and thus is considered a natural or in other words "biomass" material. Lactic acid has two optical isomers: L-lactic acid (also known as (S)-lactic acid) and D-lactic acid (also known as (R)-lactic acid), depicted as follows:

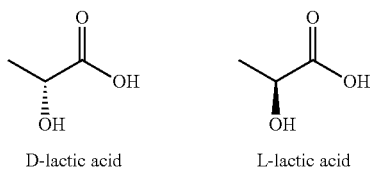

D-lactic acid    L-lactic acid

Polyesterification of lactic acid affords polylactic acid polymer.

More typically, lactic acid is typically converted to the cyclic lactide monomer, and the lactide undergoes ring opening polymerization, such as depicted as follows:

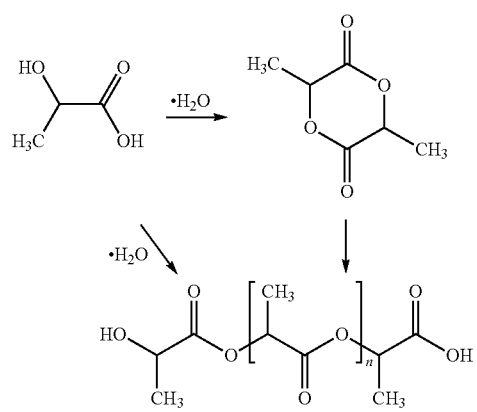

The resulting polymer material is typically referred to as polylactide polymer.

The degree of crystallinity, and hence many important properties, is largely controlled by the ratio of D and/or meso-lactide to L cyclic lactide monomer used. Likewise, for polymers prepared by direct polyesterification of lactic acid, the degree of crystallinity is largely controlled by the ratio of polymerized units derived from D-lactic acid to polymerized units derived from L-lactic acid.

The foam compositions and articles described herein generally comprise an amorphous PLA polymer alone, a semicrystalline PLA polymer alone, or both in combination. Both the semicrystalline and amorphous PLA polymers generally comprise high concentrations of polymerized units derived from L-lactic acid (e.g. L-lactide) with low concentrations of polymerized units derived from D-lactic acid (e.g. D-lactide). Or the semicrystalline and amorphous PLA polymers generally comprise high concentrations of polymerized units derived from D-lactic acid (e.g., D-lactide) with low concentrations of polymerized units derived from L-lactic acid (e.g., L-lactide).

The semicrystalline PLA polymer typically comprises at least 90, 91, 92, 93, 94, or 95 wt.-% of polymerized units derived from L-lactic acid (e.g. L-lactide) and no greater than 10, 9, 8, 7, 6, or 5 wt.-% of polymerized units derived from D-lactic acid (e.g. D-lactide and/or meso-lactide). In yet other embodiments, the semicrystalline PLA polymer comprises at least 96 wt.-% of polymerized units derived from L-lactic acid (e.g. L-lactide) and less than 4, 3, or 2 wt.-% of polymerized units derived from D-lactic acid (e.g. D-lactide and/or meso-lactide. Likewise the composition and film comprises an even lower concentration of polymerized units derived from D-lactic acid (e.g. D-lactide and/or meso-lactide) depending on the concentration of semicrystalline PLA polymer in the composition or film. For example, if the composition comprises 15 wt.-% of a semicrystalline PLA having about 2 wt.-% D-lactide and/or meso-lactide, the composition comprises about 0.3 wt.-% D-lactide and/or meso-lactide. The composition and film generally comprises no greater than 9, 8, 7, 6, 5, 4, 3, 2, 1.5, 1.0, 0.5, 0.4, 0.3, 0.2, or 0.1 wt.-% polymerized units derived from D-lactic acid (e.g. D-lactide and/or meso-lactide). Suitable examples of semicrystalline PLA include NATUREWORKS INGEO 4042D and 4032D. These polymers have been described in the literature as having molecular weight Mw of about 200,000 g/mole; Mn of about 100,000 g/mole; and a polydispersity of about 2.0.

Alternatively, the semicrystalline PLA polymer may comprises at least 90, 91, 92, 93, 94, or 95 wt.-% of polymerized units derived from D-lactic acid (e.g. D-lactide) and no greater than 10, 9, 8, 7, 6, or 5 wt.-% of polymerized units derived from L-lactic acid (e.g. L-lactide and/or meso-lactide). In yet other embodiments, the semicrystalline PLA polymer comprises at least 96 wt.-% of polymerized units derived from D-lactic acid (e.g. D-lactide) and less than 4, 3, or 2 wt.-% of polymerized units derived from L-lactic acid (e.g. L-lactide and/or meso-lactide. Likewise the film comprises an even lower concentration of polymerized units derived from L-lactic acid (e.g. L-lactide and/or meso-lactide) depending on the concentration of semicrystalline PLA polymer in the film. For example, if the film composition comprises 15 wt.-% of a semicrystalline PLA having about 2 wt.-% L-lactide and/or meso-lactide, the film composition comprises about 0.3 wt.-% L-lactide and/or meso-lactide. The film generally comprises no greater than 9, 8, 7, 6, 5, 4, 3, 2, 1.5, 1.0, 0.5, 0.4, 0.3, 0.2, or 0.1 wt.-% polymerized units derived from L-lactic acid (e.g. L-lactide and/or meso-lactide). Examples of such semicrystalline PLA are available as "SYNTERRA PDLA".

The amorphous PLA typically comprises no more than 90 wt.-% of polymerized units derived from L-lactic acid and greater than 10 wt.-% of polymerized units derived from D lactic acid (e.g. D-lactic lactide and/or meso-lactide). In some embodiments, the amorphous PLA comprises at least 80 or 85 wt.-% of polymerized units derived from L-lactic acid (e.g. L-lactide). In some embodiments, the amorphous PLA comprises no greater than 20 or 15 wt.-% of polymerized units derived from D-lactic acid (e.g. D-lactide and/or meso-lactide). A suitable amorphous PLA includes NATUREWORKS INGEO 4060D grade. This polymer has been described in the literature to have a molecular weight Mw of about 180,000 g/mole.

Alternatively, the amorphous PLA typically comprises no more than 90 wt.-% of polymerized units derived from D-lactic acid and greater than 10 wt.-% of polymerized units derived from L lactic acid (e.g. L-lactic lactide and/or meso-lactide). In some embodiments, the amorphous PLA comprises at least 80 or 85 wt.-% of polymerized units derived from D-lactic acid (e.g. D-lactide). In some embodiments, the amorphous PLA comprises no greater than 20 or 15 wt.-% of polymerized units derived from L-lactic acid (e.g. L-lactide and/or meso-lactide).

The PLA polymers are preferably "film grade" polymers, having a melt flow rate (as measured according to ASTM D1238) of no greater than 25, 20, 15, or 10 g/min at 210° C. with a mass of 2.16 kg. In some embodiments, the PLA polymer has a melt flow rate of less than 10 or 9 g/min at 210° C. The melt flow rate is related to the molecular weight of the PLA polymer. The PLA polymer typically has a weight average molecular weight (Mw) as determined by Gel Permeation Chromatography with polystyrene standards of at least 50,000 g/mol; 75,000 g/mol; 100,000 g/mol; 125,000 g/mol; 150,000 g/mol. In some embodiments, the molecular weight (Mw) is no greater than 400,000 g/mol; 350,000 g/mol or 300,000 g/mol.

The PLA polymers typically have a tensile strength ranging from about 25 to 150 MPa; a tensile modulus ranging from about 1000 to 7500 MPa; and a tensile elongation of at least 3, 4, or 5 ranging up to about 15%. In some embodiments, the tensile strength of the PLA polymer is at least 30, 40 or 50 MPa. In some embodiments, the tensile strength of the PLA polymer is no greater than 125, 100 or 75 MPa. In some embodiments, the tensile modulus of the PLA polymer is at least 1500, 2000, or 2500 MPa. In some embodiments, the tensile modulus of the PLA polymer is no greater than 7000, 6500, 6000, 5500, 5000, or 4000 MPa. Such tensile and elongation properties can be determined by ASTM D882 and are typically reported by the manufacturer or supplier of such PLA polymers.

The PLA polymers generally have a glass transition temperature, $T_g$, as can be determined by Differential Scanning calorimetry (DSC) as described in the forthcoming examples, ranging from about 50 to 65° C.

The semicrystalline PLA polymers typically have a melting point ranging from 140 to 175° C., 180° C., 185° C. or 190° C. The PLA polymer, comprising a semicrystalline PLA and/or an amorphous PLA polymer can be melt-processed at temperatures of 180° C., 190° C., 200° C., 210° C., 220° C. or 230° C.

The foam composition typically comprises a total amount of PLA polymer no greater than 90, 85, 80, 75, or 70 wt.-% of the total weight of the foam composition, and at least 10, 15, 20, or 35 wt.-% of the total weight of the foam composition.

When the composition comprises a blend of semicrystalline and amorphous PLA, the amount of semicrystalline PLA is typically at least 5, 10, 15 or 20 wt.-%, based on the total weight of the PLA polymer, second (e.g., polyvinyl acetate) polymer, and plasticizer. In some embodiments, the amount of amorphous PLA polymer ranges from 10, 15, 25 or 30 wt.-% up to 50, 55 or 60 wt.-% based on the total weight of the PLA polymer, second (e.g., polyvinyl acetate) polymer, and plasticizer. The amount of amorphous PLA polymer can be greater than the amount of crystalline polymer.

The composition further comprises a second polymer such as polyvinyl acetate polymer. The second polymer can improve the compatibility of the PLA with a plasticizer such that the plasticizer concentration can be increased without plasticizer migration (as determined by the test method).

The second (e.g., polyvinyl acetate) polymer has a $T_g$ of at least 25° C., 30° C., 35° C. or 40° C. The $T_g$ of the second (e.g., polyvinyl acetate) polymer is typically no greater than 80° C., 75° C., 70° C., 65° C., 60° C., 55° C., 50° C. or 45° C.

The second (e.g., polyvinyl acetate) polymer typically has a weight or number average molecular weight (as determined by Size Exclusion Chromatography with polystyrene standards) of at least 50,000 g/mol; 75,000 g/mol; 100,000 g/mol; 125,000 g/mol; 150,000 g/mol; 175,000 g/mol; 200,000 g/mol; 225,000 g/mol or 250,000 g/mol. In some embodiments, the molecular weight (Mw) is no greater than 2,000,000; 1,000,000 g/mol; 750,000 g/mol; 500,000 g/mol; 450,000 g/mol; 400,000 g/mol; 350,000 g/mol or 300,000 g/mol. In some embodiments, the molecular weight of the second (e.g., polyvinyl acetate) polymer is greater than the molecular weight of the PLA polymer(s). The second (e.g., polyvinyl acetate) polymer may be characterized as having a viscosity in a 10 wt. % ethyl acetate solution at 20° C. ranging from 10 to 200 mPa*s.

In some favored embodiments, the second polymer is a polyvinyl acetate polymer. The polyvinyl acetate polymer is typically a homopolymer. However, the polymer may comprise relatively low concentrations of repeat units derived from other comonomers, provided that the $T_g$ of the polyvinyl acetate polymer is within the ranges previously described. Other comonomers include for example acrylic monomers such as acrylic acid and methyl acrylate; vinyl monomers such as vinyl chloride and vinyl pyrollidone; and $C_2$-$C_8$ alkylene monomers, such as ethylene. The total concentration of repeats derived from other comonomers of the polyvinyl acetate polymer is typically no greater than 10, 9, 8, 7, 6, or 5 wt.-%. In some embodiments, the concentration of repeats derived from other comonomers of the polyvinyl acetate polymer is typically no greater than 4, 3, 2, 1 or 0.5 wt.-%. The polyvinyl acetate polymer typically has a low level of hydrolysis. The polymerized units of the polyvinyl acetate polymer that are hydrolyzed to units of vinyl alcohol is generally no greater than 10, 9, 8, 7, 6, 5, 4, 3, 2, 1 or 0.5 mol % of the polyvinyl acetate polymer.

Polyvinyl acetate polymers are commercially available from various suppliers including Wacker Chemie AG (Munich, Germany) under the trade designation VINNAPAS and from Vinavil Americas Corporation (West Chicago, Ill.) under the trade designation VINAVIL. Prior to combining with the PLA, such polyvinyl acetate polymers are often in a (e.g. white) solid powder or colorless bead form. In some embodiments, the polyvinyl acetate polymer (e.g., powder, prior to combining with the PLA polymer) is not water redispersible.

A single second (e.g., polyvinyl acetate) polymer may be utilized or a combinations of two or more second (e.g., polyvinyl acetate) polymers.

The total amount of second (e.g., polyvinyl acetate) polymer present in the composition described herein is at least about 10 wt.-% and typically no greater than about 50, 45, or 40 wt.-%, based on the total weight of the foam composition. In some embodiments, the concentration of second (e.g., polyvinyl acetate) polymer is present in an amount of at least 15 or 20 wt.-%.

In some embodiments, the foam composition has a $T_g$ of less than 30° C., 29° C., 28° C., 27° C., 26° C., 25° C., 24° C., 23° C., 22° C., 21° C., or 20° C. and does not exhibit plasticizer migration when aged at 80° C. for 24 hours (according to the test methods described in the examples). This property is attributable to the inclusion of the second (e.g., polyvinyl acetate) polymer.

The composition further comprises a plasticizer. The total amount of plasticizer in the composition typically ranges from about 5 wt.-% to about 35, 40, 45 or 50 wt.-%, based on the total weight of the foam composition (e.g., primarily the PLA polymer, second (e.g., polyvinyl acetate) polymer, and plasticizer).

Various plasticizers that are capable of plasticizing PLA have been described in the art. The plasticizers are generally a liquid at 25° C. and typically have a molecular weight ranging from about 200 g/mol to 10,000 g/mol. In some embodiments, the molecular weight of the plasticizer is no greater than 5,000 g/mol. In other embodiments, the molecular weight of the plasticizer is no greater than 4,000, 3,000, 2,000 or 1,000 g/mol. Various combinations of plasticizers may be utilized.

The plasticizer preferably comprises one or more alkyl or aliphatic esters or ether groups. Multi-functional esters and/or ethers are typically preferred. These include alkyl phosphate esters, dialkylether diesters, tricarboxylic esters, epoxidized oils and esters, polyesters, polyglycol diesters, alkyl alkylether diesters, aliphatic diesters, alkylether monoesters, citrate esters, dicarboxylic esters, vegetable oils and their derivatives, and esters of glycerine. Such plasticizers generally lack aromatic groups and halogen atoms and are anticipated to be biodegradable. Such plasticizers commonly further comprise linear or branched alkyl terminal group groups having a carbon chain length of $C_2$ to $C_{10}$.

In one embodiment, the plasticizer is a bio-based citrate-based plasticizer represented by the following Formula (I):

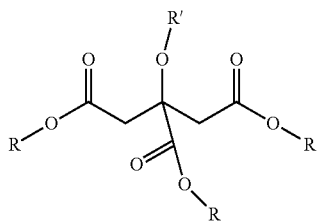

(I)

wherein
each R is independently alkyl groups that may be the same or different; and
R' is an H or an ($C_1$ to $C_{10}$) acyl group.

Each R is typically independently linear or branched alkyl groups having a carbon chain length of $C_1$ to $C_{10}$. In some embodiments, R is a $C_2$ to $C_8$ or $C_2$ to $C_4$ linear alkyl group. In some embodiments, R' is acetyl. In other embodiments, at least one R is a branched alkyl groups having a carbon chain length of $C_5$ or greater. In some embodiments, the branched alkyl group has a carbon chain length no greater than 8.

Representative citrate-based plasticizer include for example triethyl citrate, acetyl triethyl citrate, tributyl citrate, acetyl tributyl citrate, trihexyl citrate, acetyl trihexyl citrate, trioctyl citrate, acetyl trioctyl citrate, butyryl trihexyl citrate, acetyl tris-3-methylbutyl citrate, acetyl tris-2-methylbutyl citrate, acetyl tris-2-ethylhexyl citrate, and acetyl tris-2-octyl citrate.

In another embodiment, the plasticizer comprises a polyethylene glycol backbone and ester alkyl terminal groups. The molecular weight of the polyethylene glycol segment is typically at least 100, 150 or 200 g/mole and no greater than 1,000 g/mole. In some embodiments, the polyethylene glycol segment has a molecular weight no greater than 900, 800, 700, or 600 g/mole. Examples include polyethylene glycol (400) di-ethylhexonate available from Hallstar, Chicago, Ill. under the trade designation "TEGMER 809" ("TegMeR™ 809") and tetraethylene glycol di-ethylhexonate available from Hallstar, Chicago, Ill. under the trade designation "TEGMER 804" ("TegMeR™ 804").

In another embodiment, the plasticizer is a substituted or unsubstituted aliphatic polyester, such as described in U.S. Pat. No. 8,158,731; incorporated herein by reference.

In some embodiments, the aliphatic polyester plasticizer comprises repeating units derivable from succinic acid, glutaric acid, adipic acid, and/or sebacic acid. In some embodiments, the polyesters of the polymer blends disclosed herein comprise repeating units derivable from 1,3-propanediol and/or 1,2-propanediol. In some embodiments, the polyesters of the polymer blends disclosed herein comprise one or two terminator units derivable from 1-octanol, 1-decanol, and/or mixtures thereof. In some embodiments, the polyesters of the polymer blends disclosed herein comprise repeating units derivable from succinic acid, glutaric acid, adipic acid, and/or sebacic acid; repeating units derivable from 1,3-propanediol and/or 1,2-propanediol; and one or two terminator units derivable from 1-octanol, 1-decanol, and/or mixtures thereof.

In some embodiments, the aliphatic polyester plasticizer has the following formula:

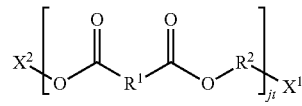

wherein n is 1 to 1000; $R^1$ is selected from the group consisting of a covalent bond and a substituted or unsubstituted aliphatic hydrocarbon group having 1 to 18 carbon atoms; $R^2$ is a substituted or unsubstituted aliphatic hydrocarbon group having 1 to 20 carbon atoms; $X^1$ is selected from the group consisting of —OH, —$O_2$C—$R^1$—$CO_2H_2$, and —$O_2$C—$R^1$—$CO_2R^3$; $X^2$ is selected from the group consisting of —H, —$R^2$—OH, and $R^3$; and $R^3$ is a substituted or unsubstituted aliphatic hydrocarbon group having 1 to 20 carbon atoms. In some embodiments, the polyester has the above formula with the proviso that if $X^1$ is —OH or —$O_2$C—$R^1$—$CO_2H$, then $X^2$ is $R^3$.

The number of repeat units n is selected such that the aliphatic polyester plasticizer has the previously described molecular weight.

In some embodiments, $R^1$, $R^2$, and/or $R^3$ are alkyl groups. $R^1$ alkyl groups can have, for example, from 1 to 18 carbon atoms, from 1 to 10 carbon atoms, from 1 to 8 carbon atoms, from 2 to 7 carbon atoms, from 2 to 6 carbon atoms, from 2 to 5 carbon atoms, from 2 to 4 carbon atoms, and/or 3 carbon atoms. $R^1$, for example, can be selected from the group consisting of —$(CH_2)_2$—, —$(CH_2)_3$—, —$(CH_2)_4$—, and —$(CH_2)_8$—. $R^2$ alkyl groups can have, for example, from 1 to 20 carbon atoms, from 1 to 10 carbon atoms, from 1 to 8 carbon atoms, from 2 to 7 carbon atoms, from 2 to 6 carbon atoms, from 2 to 5 carbon atoms, from 2 to 4 carbon atoms, and/or 3 carbon atoms. $R^2$, for example, can be selected from the group consisting of —$(CH_2)_3$—, —$CH_2CH(CH_3)$—, and —$CH(CH_3)CH_2$—. $R^3$ alkyl groups can have, for example, from 1 to 20 carbon atoms, from 1 to 18 carbon atoms, from 2 to 16 carbon atoms, from 3 to 14 carbon atoms, from 4 to 12 carbon atoms, from 6 to 12 carbon atoms, from 8 to 12 carbon atoms, and/or from 8 to 10 carbon atoms. $R^3$, for example, also can be a mixture comprising —$(CH_2)_7CH_3$ and —$(CH_2)_9CH_3$.

In some embodiments, $R^1$ is an alkyl group having from 1 to 10 carbons, $R^2$ is an alkyl group having from 1 to 10 carbons, and $R^3$ is an alkyl group having from 1 to 20 carbons. In other embodiments, $R^1$ is an alkyl group having from 2 to 6 carbons, $R^2$ is an alkyl group having from 2 to 6 carbons, and $R^3$ is an alkyl group having from 8 to 12 carbons. In still other embodiments, $R^1$ is an alkyl group having from 2 to 4 carbons, $R^2$ is an alkyl group having from 2 to 3 carbons, and $R^3$ is an alkyl group having from 8 to 10 carbons. In yet other embodiments, $R^1$ is selected from the group consisting of —$(CH_2)_2$—, —$(CH_2)_3$—, —$(CH_2)_4$—, and —$(CH_2)_8$—, $R^2$ is selected from the group consisting of —$(CH_2)_3$—, —$CH_2CH(CH_3)$—, and —$CH(CH_3)CH_2$—, and $R^3$ is a mixture comprising —$(CH_2)_7CH_3$ and —$(CH_2)_9CH_3$.

The aliphatic polyester plasticizer can have an acid value of about zero to about 20, or greater. The acid value of the polyesters can be determined by known methods for measuring the number of milligrams of potassium hydroxide necessary to neutralize the free acids in one gram of polyester sample.

Plasticizer with a low acid value is typically preferred for the shelf-life stability and/or durability of the foam. In some embodiments, the acid value of the plasticizer is preferably no greater than 10, 9, 8, 7, 6, 5, 4, 3, 2 or 1.

The aliphatic polyester plasticizer can have a hydroxyl value of about zero to about 110, for example, about 1 to about 40, about 10 to about 30, about 15 to about 25, about 30 to about 110, about 40 to about 110, about 50 to about 110, and/or about 60 to about 90. The polyesters also can have a hydroxyl value greater than about 110. The hydroxyl value of the polyesters can be determined by known methods for measuring hydroxyl groups, such as the methods described by ASTM Test Method D 4274.

One representative aliphatic polyester plasticizer is available from Hallstar, Chicago, Ill., as the trade designation HALLGREEN R-8010. In some embodiments, the plasticizer compound typically has little or no hydroxyl groups. In some embodiments, the wt.-% percent of hydroxyl groups relative to the total weight of the plasticizer compound is no greater than 10, 9, 6, 7, 6, 5, 4, 3, 2, 1 wt.-%. In some embodiments the plasticizer compound contains no hydroxyl groups. Thus, in this embodiment, the plasticizer is not glycerol or water.

The low molecular weight of commercially available PLA polymers has been known to impede the generation of PLA foams because the melt viscosity of the polymer is too low. It has been discovered that the properties of foam system based on PLA can be further controlled through the addition of one or more of crosslinking agents, crosslink catalysts, nucleating agents, and/or cell stabilizers. Once modified, at least some of these foam systems can be extruded or molded into parts with desired properties.

Suitable crosslinking agents (e.g., crosslinkers) are often low molecular weight polymers that contain multiple acid or alcohol reactive functionality, such as reactive polymers comprising a functional group selected from epoxide, anhydride, oxazoline, isocyanate, azlactone, aziridine, and combinations thereof. When used, the crosslinking agent is present in an amount of at least 0.005 wt.-%, at least 0.01, at least 0.025, at least 0.05, at least 0.1, at least 0.25, at least 0.5, at least 1.0, or at least 2.0 wt.-%, based on the total weight of the foam composition; and up to 5.0 wt.-%, up to 4.5, up to 4.0, up to 3.5, up to 3.0, or up to 2.5, or up to 1.0, or up to 0.5 wt.-%, based on the total weight of the foam composition. Stated another way, in certain embodiments, the crosslinking agent is present in an amount ranging from 0.005 to 5.0 weight percent, inclusive, ranging from 0.005 to 3.0 weight percent, inclusive, ranging from 0.005 to 0.5 weight percent, inclusive, ranging from 0.01 to 1.0 weight percent, inclusive, or ranging from 0.75 to 5.0 weight percent, inclusive, based on the total weight of the foam composition. Useful crosslinking agents (e.g., crosslinkers) include for instance and without limitation the "JONCRYL ADR" chain extenders available from BASF Corporation (Sturtevant, Wis.), for example under the trade designations "JONCRYL ADR 4300", "JONCRYL ADR 4370", "JONCRYL ADR 4380", "JONCRYL ADR 4385", and "JONCRYL ADR 4368"; and an oxazoline functionalized polymer available from Nippon Shokubai (Osaka, Japan) under the trade designation "EPOCROS RPS-1005".

It has been found that the speed of crosslinking the foam composition affects the ability to prepare foam compositions having specific cell sizes and shapes. More particularly, in certain embodiments, the foam composition further comprises a crosslink catalyst to increase the rate of crosslinking as compared to the rate of crosslinking in the absence of the crosslink catalyst. In some embodiments, the crosslink catalyst is present in an amount of at least 0.005 wt.-%, at least 0.01, at least 0.025, at least 0.05, at least 0.1, at least 0.25, at least 0.5, or at least 0.75 wt.-%, based on the total weight of the foam composition; and up to 2.50 wt.-%, up to 2.25, up to 2.0, up to 1.75, up to 1.5, up to 1.25, or up to 1.0 wt.-%, based on the total weight of the foam composition. Stated another way, in certain embodiments, the crosslink catalyst is present in an amount ranging from 0.005 to 2.50 weight percent, inclusive, ranging from 0.005 to 1.0 weight percent, inclusive, ranging from 0.005 to 0.5 weight percent, inclusive, ranging from 0.01 to 1.0 weight percent, inclusive, or ranging from 0.75 to 2.50 weight percent, inclusive, based on the total weight of the foam composition.

In certain embodiments, the crosslink catalyst comprises an alkyl or alkenyl ammonium, phosphonium, or imidizolium salt. Useful crosslink catalysts include for instance and without limitation crosslink catalysts of formula (I), (II), (III), or (IV):

$$Q(R^1)_4X \quad (I);$$

$$QR^1(R^2)_3X \quad (II);$$

$$QR^3(R^2)_3X \quad (II);$$

$$Q(R^3)_3R^1X \quad (IV);$$

wherein Q is nitrogen or phosphorous; $R^1$ is a $C_1$-$C_{20}$ alkyl or alkenyl group; $R^2$ is a $C_1$-$C_8$ alkyl or alkenyl group; $R^3$ is a phenyl group, a benzyl group, or a polycyclic aromatic hydrocarbon group; and X is an anion selected from bromide, iodide, chloride, acetate, sulfate, carbonate, phosphate, tosylate, or hexafluorophosphase. In certain embodiments, Q is N; $R^1$ is a $C_1$-$C_{12}$ alkyl group; $R^2$ is a $C_1$-$C_8$ alkyl group; $R^3$ is a phenyl group; and X is an anion selected from bromide, iodide, or chloride. Some suitable crosslink catalysts include, for example, dodecyltrimethylammonium bromide, tetrabutylammonium bromide, tetrabutylammonium iodide, tetraoctylammonium bromide, tetrabutylammonium chloride, and triphenyl monoalkyl phosphonium salts.

Such crosslink catalysts as described above were unexpectedly discovered to assist in causing the composition to crosslink at least partially concurrently with the foaming of the composition.

In certain embodiments, the foam composition further comprises a blowing agent comprising a plurality of expandable microspheres. The blowing agent is present in an amount ranging from 0.1 to 10 weight percent, inclusive, based on the total weight of the foam composition. An "expandable microsphere" refers to a microsphere that includes a polymer shell and a core material in the form of a gas, liquid, or combination thereof, which expands upon heating. Expansion of the core material, in turn, causes the shell to expand, at least at the heating temperature. An expandable microsphere is one where the shell can be initially expanded or further expanded without breaking. Some microspheres may have polymer shells that only allow the core material to expand at or near the heating temperature. Hence, during the formation of the foam composition, at least some of the expandable microspheres will expand and form cells in the foam. Suitable expandable microspheres include for instance and without limitation, those available from Pierce Stevens (Buffalo, N.Y.) under the designations "F30D", "F80SD", and "F100D"; and from Akzo-Nobel (Sundsvall, Sweden) under the designations "Expancel 551", "Expancel 461", "Expancel 091", and "Expancel 930". Each of these microspheres features an acrylonitrile-containing shell.

To facilitate the rate of crystallization, a PLA crystallization nucleating agent may also be present in the PLA foam composition. A crystallization nucleating agent generally enhances the initiation of crystallization sites and induces crystallization of the polymeric material, thereby increasing the rate of crystallization. Additionally, a cell nucleating agent generally provides initiating sites at which a blowing agent forms voids in a foam composition. By selection of the cell nucleating agent, void sizes in the foam are better controlled (e.g., made smaller or larger), as compared to without including the nucleating agent. Typically, when used, the one or more nucleating agents (e.g., crystallization and/or cell nucleating agents) are present in an amount ranging from 0.1 to 15 weight percent, inclusive, based on the total weight of the foam composition.

Suitable nucleating agent(s) include for example inorganic minerals, organic compounds, salts of organic acids and imides, finely divided crystalline polymers with a melting point above the processing temperature of PLA, and combinations of two or more of the foregoing. Combinations of two or more different nucleating agents may also be used.

Examples of useful crystallization nucleating agents include, for example, talc (hydrated magnesium silicate—$H_2Mg_3(SiO_3)_4$ or $Mg_3Si_4O_{10}(OH)_2$), silica ($SiO_2$), titania ($TiO_2$), alumina ($Al_2O_3$), zinc oxide, sodium salt of saccharin, calcium silicate, sodium benzoate, calcium titanate, aromatic sulfonate derivative, boron nitride, copper phthalocyanine, phthalocyanine, sodium salt of saccharin, isotactic polypropylene, polybutylene terephthalate, and the like.

When an organic crystallization nucleating agent is present, the nucleating agent is typically at a concentration of at least 0.01, 0.02, 0.03, 0.04, 0.05, 0.1, 0.15 or 0.2 wt.-% ranging up to about 1, 2, 3, 4 or 5 wt.-% based on the total weight of the composition. When the nucleating agent is an inorganic oxide filler such as silica, alumina, zinc oxide, and talc, the concentration can be higher.

In one embodiment, the crystallization nucleating agent may be characterized as a salt of a phosphorous-containing aromatic organic acid such as zinc phenylphosphonate, magnesium phenylphosphonate, disodium 4-tert-butylphenyl phosponate, and sodium diphenylphosphinates.

One favored crystallization nucleating agent is zinc phenylphosphonate having the following chemical formula:

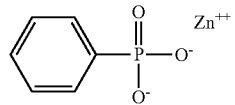

available from Nissan Chemical Industries, Ltd under the trade designation "Ecopromote".

Examples of useful cell nucleating agents include, for example, talc, silica, silica particles functionalized with organic groups (e.g., an octyl silane, a polyethylene glycol silane), glass beads, polymer particles (e.g., starch (such as hydroxypropyl starch), polystyrene, polyvinyl pyrollidone (PVP)), mica, alumina, clay, calcium silicate, calcium titanate, calcium carbonate, and titania.

The foam compositions and articles may optionally contain one or more conventional additives. Additives include, for example, antiblock additives, cell stabilizers, surfactants, antioxidants, ultraviolet absorbers, lubricants, processing aids, antistatic agents, colorants, impact resistance aids, fillers, matting agents, flame retardants (e.g. zinc borate), pigments, and the like.

Suitable cell stabilizers include for instance and without limitation erucamide (i.e., (Z)-13-Docosenamide), and surface modified silica nanoparticles. Surface modified silica nanoparticles may be functionalized with an octyl silane or a polyethylene glycol silane, for example. In certain embodiments, additional suitable surface modified silica nanoparticles include those described in U.S. Pat. No. 6,586,483 (Kolb et al.).

In some embodiments, inorganic fillers may be used as antiblock additives to prevent blocking or sticking of layers or rolls of the film during storage and transport. Inorganic fillers include clays and minerals, either surface modified or not. Examples include talc, diatomaceous earth, silica, mica, kaolin, titanium dioxide, perlite, and wollastonite.

Hence, certain materials may potentially act as more than one of a crystallization nucleating agent, a cell nucleating agent, an antiblock additive, a cell stabilizer, etc., in a foam composition.

Organic biomaterial fillers include a variety of forest and agricultural products, either with or without modification. Examples include cellulose, wheat, starch, modified starch, chitin, chitosan, keratin, cellulosic materials derived from agricultural products, gluten, flour, and guar gum. The term "flour" concerns generally a composition having protein-containing and starch-containing fractions originating from one and the same vegetable source, wherein the protein-containing fraction and the starch-containing fraction have not been separated from one another. Typical proteins present in the flours are globulins, albumins, glutenins, secalins, prolamins, glutelins. In typical embodiments, the composition comprises little or no organic biomaterial fillers such a flour. Thus, the concentration of organic biomaterial filler (e.g. flour) is typically less than 10, 9, 8, 7, 6, 5, 4, 3, 2, or 1 wt.-% of the total foam composition.

Advantageously, the foam compositions according to at least certain embodiments of the present disclosure provide cell shapes and sizes similar to those obtainable in PVC foam compositions. In some embodiments, for example, the foam cells have an average diameter of at least 1 micrometer (μm), at least 5 μm, at least 10 μm, at least 25 μm, at least 50 μm, at least 100 μm, and up to 10 millimeters (mm), up to 8 mm, up to 6 mm, up to 4 mm, up to 2 mm, up to 1 mm, up to 750 μm, up to 500 μm, or up to 250 μm. Stated another way, the foam cells can have an average diameter ranging from 1 μm to 3 millimeters, inclusive, ranging from 1 μm to 50 μm, inclusive, ranging from 1 μm to 10 μm, inclusive, ranging from 1 μm to 1 mm, inclusive, or ranging from 50 μm to 10 mm, inclusive. Moreover, in some embodiments, the foam cells exhibit a roundness ranging from 1.0 to 2.0, inclusive, ranging from 1.0 to 1.5 inclusive, or ranging from 1.55 to 2.0, inclusive.

In certain embodiments, the foam composition comprises a blown foam composition. It was surprisingly discovered that at least some embodiments of blown foam compositions provide a surface writable by pen and/or pencil, and similarly are printable with ink. This is in contrast to a PLA/PVAc film of the same composition that has not been blown into a foam, which tends to have a surface morphology that is smooth and slippery. Stated another way, in some embodiments, the foam composition comprises a rough surface morphology, which facilitates the writability of the foam composition.

In a third aspect, a foam sheet is provided. The foam sheet includes the foam composition according to the first aspect (e.g., closed cell foam) or the second aspect (e.g., open celled foam).

Preparing a foam composition in the form of a sheet provides for use of the foam composition in thermal and acoustic insulation applications.

When the foam composition is a monolithic sheet, the thickness of the sheet is typically at least 25, 50, or 100 μm (4 mils) to 500 μm (20 mils) thickness. In some embodiments, the thickness of the foam sheet is no greater than 10 mm, 5 mm, 2 mm, 400 μm, 300 μm, or 200 μm. The foam may be in the form of individual sheets, particularly for a thickness of greater than 20 mils. The (e.g., thinner) foam may be in the form of a roll-good.

In a fourth aspect, a method of making a foam composition is provided. The method includes compressing a mixture comprising a polylactic acid polymer; a second (e.g., polyvinyl acetate) polymer having a $T_g$ of at least 25° C.; a plasticizer; and a blowing agent; and heating the compressed mixture, thereby forming the foam composition.

In preparing a composition as described herein, the PLA, polyvinyl acetate polymer, plasticizer, and one or more optional ingredients including crosslinking agent, crosslink catalyst, nucleating agent, etc., are heated (e.g., subjected to a temperature ranging from 180° C.-250° C., inclusive) and thoroughly mixed using any suitable means known by those of ordinary skill in the art. For example, the composition may be mixed by use of a (e.g., Brabender) mixer, extruder, kneader or the like.

The composition generally has a glass transition temperature ranging from about −20° C., −15° C., or −10° C. to 40° C.; below the $T_g$ of both the PLA polymer and the second (e.g., polyvinyl acetate) polymer. In some embodiments, the composition has a glass transition temperature of at least −5° C., −4° C., −3° C., −2° C., −1° C. or 0° C. In some embodiments, the composition has a glass transition temperature of less than 35° C. or 30° C. or 25° C. In some embodiments, the composition has a glass transition temperature of less than 20° C., 19° C., or 18° C. The composition typically has a melting temperature, $T_m$, ranging from of at least about 150° C. or 155° C. to about 165° C., 170° C., 175° C., 180° C., 185° C., or 190° C. Further, the composition can have a crystallization peak temperature $T_c$ ranging from 80° C. to 140° C.

The net melting endotherm is the energy of the melting endotherm less the energy of the crystallization exotherm. The net melting endotherm of the mixtures is determined by the second heating scan; whereas the net melting endotherm of a (e.g., melt pressed) film is determined by the first heating scan. According to U.S. Pat. No. 6,005,068, a PLA film is considered to be amorphous if it exhibits a net melting endotherm of less than about 10 J/g. In favored embodiments, such as when the composition and film comprises a nucleating agent, the net melt enthalpy of the composition and film, $\Delta H_{nm2}$ and $\Delta H_{nm1}$, respectively, is greater than 10, 11, 12, 13, 14 or 15 J/g and less than 40, 39, 38, 37, 36 or 35 J/g.

In certain embodiments, the mixture may be prepared into the form of pellets, such as by extruding and pelletizing at least a portion of the mixture. One advantage to the mixture comprising a plurality of pellets is a greater ease of handling the mixture than certain alternate forms of mixtures.

Upon heating the mixture, the blowing agent assists in generating voids to form the foam composition. In some embodiments, the blowing agent comprises a chemical blowing agent, a physical blowing agent, or a combination thereof (e.g., more than one blowing agent may be used in certain foam compositions). Useful categories of blowing agents include, for instance, a volatile liquid, a gas, a chemical compound, and a plurality of expandable microspheres. Volatile liquid and gas blowing agents tend to escape from the mixture, leaving voids behind, to form the foam composition. Chemical compound blowing agents decompose and at least a portion of the decomposition product(s) escape from the mixture, leaving voids behind. In some embodiments, the blowing agent comprises a plurality of expandable microspheres, which are described above.

Suitable chemical blowing agents include for instance and without limitation, a synthetic azo-based compound, a carbonate-based compound, a hydrazide-based compound, and combinations thereof. Useful specific compounds include, for example, 1,1-azodicarbonamide, azodiisobutyro-nitrile, benzenesulfonhydrazide, and hydrazo dicarbonamide. In contrast, endothermal chemical blowing agents were found to be too reactive to effectively form a foam composition from the mixture.

In embodiments in which the blowing agent comprises a gas, suitable blowing agents comprises carbon dioxide. It has been found that a gas blowing agent (e.g., carbon dioxide) may be incorporated into the mixture at a pressure ranging from 300 psi (2.07 MPa) to 10,000 psi (68.95 MPa), inclusive. When used, the gas blowing agent is typically incorporated into the mixture by soaking into the mixture for at least 1 minute, at least 2 minutes, at least 5 minutes, at least 10 minutes, or at least 15 minutes.

Despite issues with having lower melt viscosities than other polymers typically used to form foam compositions, the foam compositions according to at least certain embodiments of the present disclosure may be processed to prepare blown foam compositions. In certain embodiments, the method of forming a foam composition comprises blowing the mixture to form a blown foam composition, for instance employing a blown film line. Blown foam compositions may be prepared having a density that is less than half of the density of a film of the same composition.

Various methods for preparing foam compositions are suitable for at least certain embodiments of the method. More particularly, the method may include compressing the mixture in a melt press and/or an extruder, and may include heating the compressed mixture in a mold, an oven, and/or an extruder. In certain embodiments, the mixture is compressed in an extruder, heated in an extruder, or both compressed and heated in an extruder. The compressed mixture is heated, typically by subjection to a temperature of at least 130° C., at least 140° C., at least 150° C., at least 160° C., or at least 170° C.; and up to 210° C., up to 200° C., up to 190° C., or up to 180° C.; such as ranging from 130° C. and 210° C., inclusive.

In a fifth aspect, another method of making a foam composition is provided. The method comprises subjecting a mixture to an elevated pressure; and diffusing a gas into the mixture, followed by ending the subjection to the elevated pressure, thereby forming the foam composition. The mixture includes a polylactic acid polymer; a second (e.g., polyvinyl acetate) polymer having a $T_g$ of at least 25° C.; and a plasticizer. In many embodiments, the elevated pressure is at least 300 psi (2.07 MPa), at least 500 psi (3.45 MPa), at least 750 psi (5.17 MPa), at least 1,000 psi (6.89 MPa), at least 2,500 psi (17.24 MPa), or at least 4,000 psi (27.58 MPa); and up to 10,000 psi (68.95 MPa), up to 8,000 psi (55.16 MPa), up to 6,000 psi (41.37 MPa), or up to 5,000 psi (34.47 MPa); and ranges from 300 psi (2.07 MPa) to 10,000 psi (68.95 MPa), inclusive. Suitable gases include carbon dioxide. Optionally, the mixture further comprises at least one physical blowing agent, such as a volatile liquid and/or expandable microspheres.

In certain embodiments, the gas is diffused into the mixture in an extruder. Generally, the gas is diffused into the mixture by soaking into the mixture for at least 1 minute, at least 2 minutes, at least 5 minutes, at least 10 minutes, or at least 15 minutes. The method often further includes heating the mixture, such as by subjecting the mixture to a temperature detailed above with respect to the fourth aspect.

The PLA foam compositions described herein can be used in a variety of products. In some embodiments, the PLA foam composition has similar or even better properties to polyvinyl chloride (PVC) foam compositions, and thus can be used in place of PVC foams.

The foam compositions can have various properties, as determined by the test methods set forth in the examples, including cell size and homogeneity, cell roundness, foam composition density, compression modulus, and max torque (e.g., extent of crosslinking).

In a sixth aspect, a hearing protection article is provided. The hearing protection article includes the foam composition according to the first aspect or the second aspect.

In a seventh aspect, a process is provided. The process includes providing at least one hearing protection article according to the sixth aspect; and interposing the hearing protection article between an acoustic source and an acoustic receiver in the form of a human ear.

Hearing protection articles suitable for use in the process of the seventh aspect include those that comprise at least one of the above-described hearing protection articles. In certain embodiments, the hearing protection articles further comprise at least one casing that at least partially encloses the sound barrier and is adapted for contact (direct or indirect) with the human ear. For instance, the hearing protection device can be an acoustic earmuff or an acoustic earplug. Various configurations of earplugs are known, that could be made employing foam compositions according to the present disclosure, for instance, suitable earplugs include those illustrated in FIGS. 7A-9B.

Figure 7A:
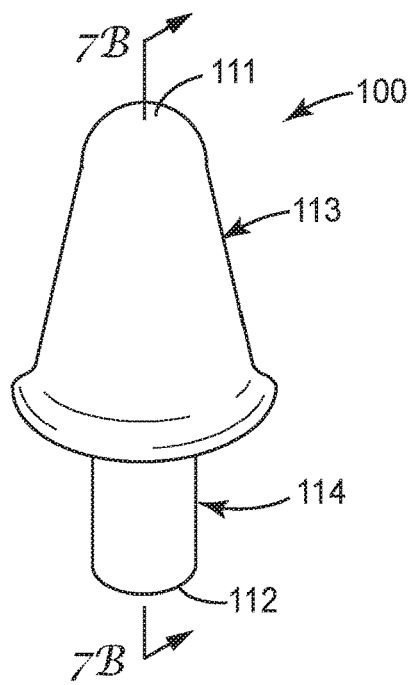
FIG. 7A is a perspective view of an exemplary earplug according to the present disclosure.
Figure 7B:
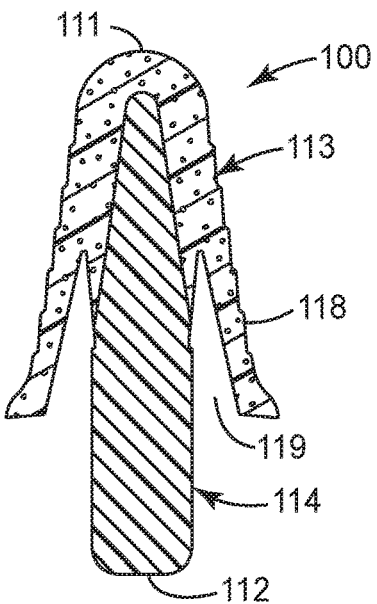
FIG. 7B is a cross-sectional view of the earplug of FIG. 7A.

Referring to FIGS. 7A-7B, an exemplary push-to-fit type earplug 100 is shown. In an exemplary embodiment, the earplug 100 includes a body made entirely of closed cell foam. The body has a first end 111 and a second end 112, and includes a sound attenuating portion 113 and a semi-rigid stem portion 114. The stem portion 114 is partially surrounded by sound attenuating portion 113, and is partially exposed to allow a user to grasp the stem portion 114 to handle the earplug 100 and to facilitate insertion of the earplug 100 into an ear canal of a user. In this embodiment, the stem portion 114 does not extend to the first end 111 and only the sound attenuating portion 113 is present at the first end 111. Optionally, the sound attenuating portions 113 may include a flange 118 extending outwardly and defining a flange cavity 119. The flange 118 may collapse inwardly into the flange cavity 119 upon insertion into an ear canal of a user. In many embodiments, at least the sound attenuating portion 113 is composed of foam compositions according to the present disclosure.

Figure 8A:
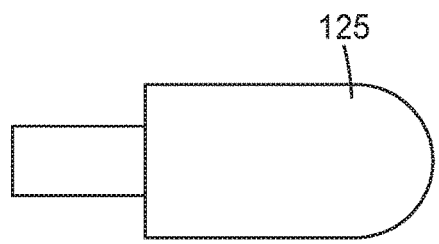
FIG. 8A is a side view of another exemplary earplug according to the present disclosure.
Figure 8B:
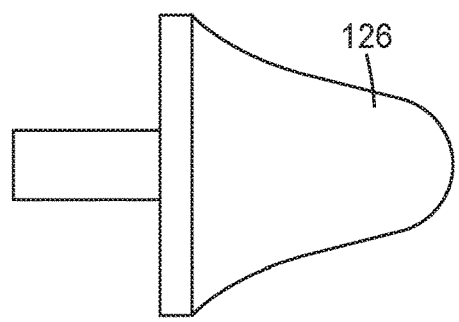
FIG. 8B is a side view of further exemplary earplug according to the present disclosure.
Figure 9A:
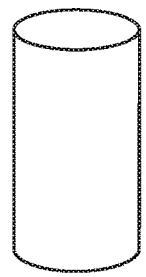
FIG. 9A is a side view of yet another exemplary earplug according to the present disclosure.
Figure 9B:
FIG. 9B is a side view of a still further exemplary earplug according to the present disclosure.

Referring to FIGS. 8A and 8B, in various other embodiments, for example, the sound attenuating portions 125, 126, respectively, may be hemisphere-shaped, bullet-shaped, or otherwise shaped to provide a desired fit or to suit a particular application. Referring to FIGS. 9A and 9B, in certain embodiments, the earplug does not include a stem, but rather has a cylindrical shape (i.e., FIG. 9A) or a cylindrical shape with a rounded end (i.e., FIG. 9B).

Figure 10:
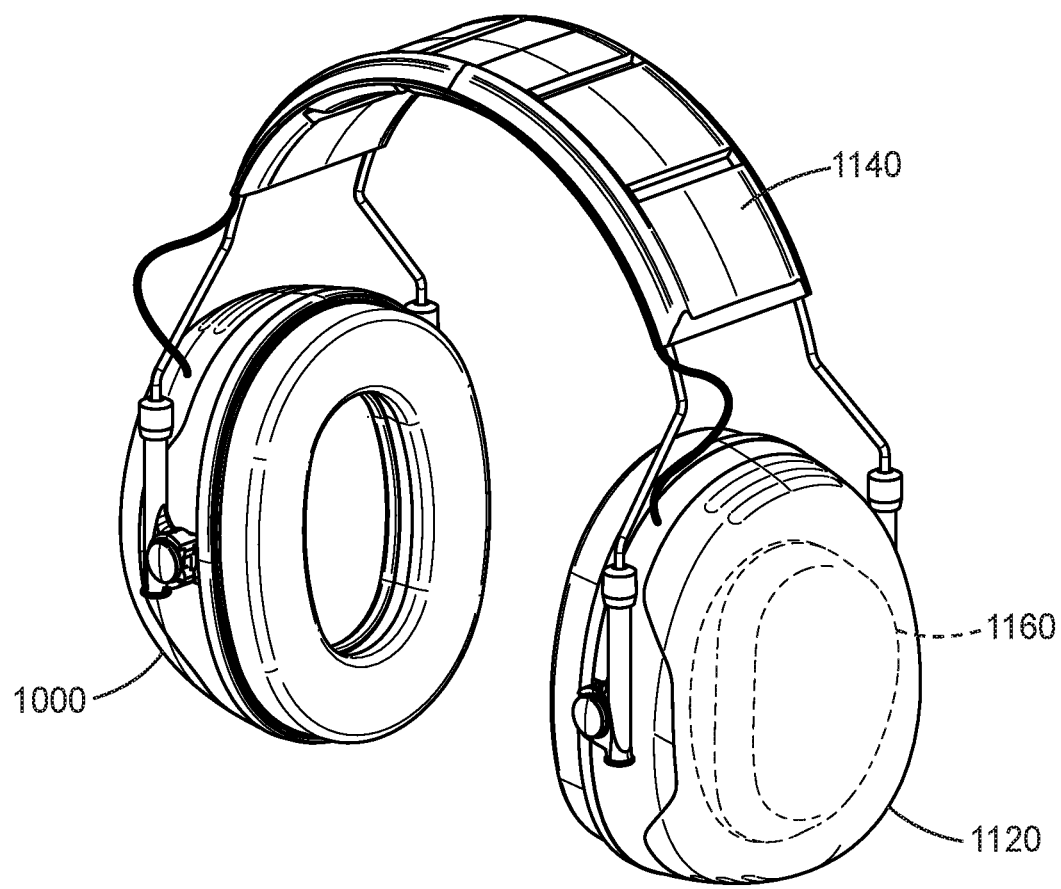
FIG. 10 is a perspective view of an exemplary earmuff according to the present disclosure.

Useful acoustic earmuffs include those that comprise (a) a connecting band having opposing first and second ends; and (b) a pair of earmuff cup assemblies connected to the opposing first and second ends of the connecting band, each earmuff cup assembly comprising at least one of the above-described foam compositions as sound barriers (and thus serving as a casing for the sound barrier). The connecting band can be, for example, a generally U-shaped band made of a flexible and/or resilient material (for example, two resilient wires held in substantially parallel alignment by a strip of flexible material such as a rubber or a plastic). The earmuff cup assembly can comprise, for example, an earcup (for example, a rigid earcup), the sound barrier, and, optionally, an earmuff cushion (for example, a polymer foam) and/or an earmuff cup liner (for example, an open celled polymer foam). The earmuff cup assemblies can be attached to the connecting band in essentially any desired manner. For instance, referring to FIG. 10, an exemplary earmuff includes a second protective muff 1120 connected to a first protective muff 1000 by a bridging portion 1140. The second protective muff 1120 is illustrated to house at least a portion of the foam composition 1160 contained in the earmuff.

Other hearing protection articles (for example, acoustic earplugs suitable for insertion in the human ear) and other types or designs of acoustic earmuffs also can be used in carrying out the process. The sound barrier can be directly or indirectly attached to or suspended within the casing of the hearing protection article by essentially any known or hereafter-developed method (for example, use of adhesives, mechanical fasteners, form-fitting, and/or the like) that does not unacceptably disrupt or alter the substantial periodicity of the sound barrier or its acoustical characteristics.

The hearing protection article can be used in the hearing protection or sound insulation process of the invention by interposing or placing the hearing protection device between an acoustic source (preferably, a source of audible acoustic frequencies) and an acoustic receiver in the form of a human ear (a receiver of audible acoustic frequencies; preferably, in a manner such that the receiver is completely covered by the device). Useful acoustic sources include industrial noise, construction noise, recreational noise, music, and the like (preferably, noises or other sounds having an audible component; more preferably, noises or other sounds having a frequency component in the range of about 63 Hz to about 16 kHz). The hearing protection article can be positioned between the source and the receiver such that a major face of the sound barrier of the article intercepts and thereby attenuates sound waves passing from the source to the receiver.

Those skilled in the art will be familiar with a variety of ways in which such articles can be so positioned. Normal incidence of the sound waves (relative to a major face of the sound barrier of the device) is generally preferred, although field incidence conditions (random orientation) can also provide reasonably effective acoustical attenuation (for example, with increases of no more than about 5 dB in transmission, relative to normal incidence conditions, when a one-dimensional, multi-layer sound barrier is utilized).

The hearing protection process and article of the present disclosure can be used to achieve transmission loss across a relatively large portion of the audible range (with preferred embodiments providing a transmission loss that across the range of about 20 Hz to about 20 kHz. Such transmission losses can be achieved while maintaining phononic crystal structure dimensions on the order of centimeters or less (preferably, less than or equal to about 20 cm; more preferably, on the order of millimeters or less; most preferably, on the order of about 1 to about 3 mm). The material stiffness, density and porosity of at least certain embodiments of the hearing protection article according to the present disclosure are useful for one or more hearing protection applications.

Various embodiments are provided that include foam compositions, articles, and methods of making and using same.

Embodiment 1 is a foam composition. The foam composition includes a polylactic acid polymer; a second polymer having a $T_g$ of at least 25° C.; and a plasticizer. The foam composition comprises a closed cell foam.

Embodiment 2 is the foam composition of embodiment 1, wherein the polylactic acid polymer comprises an amorphous polylactic acid polymer.

Embodiment 3 is the foam composition of embodiment 1 or embodiment 2, wherein the polylactic acid polymer comprises a semicrystalline polylactic acid polymer.

Embodiment 4 is the foam composition of any of embodiments 1 to 3, further including a blowing agent comprising a plurality of expandable microspheres.

Embodiment 5 is the foam composition of embodiment 4, wherein the blowing agent is present in an amount ranging from 0.1 to 10 weight percent, inclusive, based on the total weight of the foam composition.

Embodiment 6 is the foam composition of any of embodiments 1 to 5, wherein the second polymer comprises polyvinyl acetate.

Embodiment 7 is the foam composition of any of embodiments 1 to 6, further including at least one nucleating agent selected from a cell nucleating agent, a crystallization nucleating agent, and a combination thereof.

Embodiment 8 is the foam composition of embodiment 7, wherein the nucleating agent is present in an amount ranging from 0.1 to 15 weight percent, inclusive, based on the total weight of the foam composition.

Embodiment 9 is the foam composition of any of embodiments 1 to 8, further including a crosslinking agent.

Embodiment 10 is the foam composition of embodiment 9, wherein the crosslinking agent is present in an amount ranging from 0.005 to 5.0 weight percent, inclusive, based on the total weight of the foam composition.

Embodiment 11 is the foam composition of embodiment 9 or embodiment 10, wherein the crosslinking agent comprises a reactive polymer comprising a functional group selected from epoxide, anhydride, oxazoline, isocyanate, azlactone, aziridine, and combinations thereof.

Embodiment 12 is the foam composition of any of claims 1 to 11, further including a crosslink catalyst.

Embodiment 13 is the foam composition of embodiment 12, wherein the crosslink catalyst is present in an amount ranging from 0.005 to 2.50 weight percent, inclusive, based on the total weight of the foam composition.

Embodiment 14 is the foam composition of embodiment 12 or embodiment 13, wherein the crosslink catalyst comprises an alkyl or alkenyl ammonium, phosphonium, or imidizolium salt.

Embodiment 15 is the foam composition of any of embodiments 12 to 14, wherein the crosslink catalyst is of formula (I), (II), (III), or (IV):

$$Q(R^1)_4 X \qquad (I);$$

$$QR^1(R^2)_3 X \qquad (II);$$

$$QR^3(R^2)_3 X \qquad (III);$$

$$Q(R^3)_3 R^1 X \qquad (IV).$$

Wherein Q is nitrogen or phosphorous; $R^1$ is a $C_1$-$C_{20}$ alkyl or alkenyl group; $R^2$ is a $C_1$-$C_8$ alkyl or alkenyl group; $R^3$ is a phenyl group, a benzyl group, or a polycyclic aromatic hydrocarbon group; and X is an anion selected from bromide, iodide, chloride, acetate, sulfate, carbonate, phosphate, tosylate, or hexafluorophosphase.

Embodiment 16 is the foam composition of any of embodiments 1 to 15, further including an antiblock additive, a cell stabilizer, a surfactant, or a combination thereof.

Embodiment 17 is the foam composition of embodiment 16, wherein the cell stabilizer comprises silica nanoparticles functionalized with a polyethylene glycol silane.

Embodiment 18 is the foam composition of any of embodiments 1 to 16, wherein the plasticizer is present in an amount ranging from 5 to 35 weight percent, inclusive, based on the total weight of the foam composition.

Embodiment 19 is the foam composition of any of embodiments 1 to 18, wherein the second polymer is present in an amount ranging from 10 to 50 weight percent, inclusive, based on the total weight of the composition.

Embodiment 20 is the foam composition of any of embodiments 1 to 19, wherein the polylactic acid polymer is present in an amount ranging from 20 to 80 weight percent, inclusive, based on the total weight of the composition.

Embodiment 21 is the foam composition of any of embodiments 1 to 20, wherein the composition has a $T_g$ (defined by DSC) less than 30° C., 25° C. or 20° C.

Embodiment 22 is the foam composition of any of embodiments 1 to 20, wherein the composition does not exhibit plasticizer migration when aged at 80° C. for 24 hours.

Embodiment 23 is the foam composition of any of embodiments 1 to 22, wherein the foam cells have an average diameter ranging from 1 μm to 10 millimeters, inclusive.

Embodiment 24 is the foam composition of any of embodiments 1 to 23, wherein the foam cells exhibit a roundness ranging from 1.0 to 2.0, inclusive.

Embodiment 25 is the foam composition of any of embodiments 1 to 24, wherein the foam composition comprises a rough surface morphology.

Embodiment 26 is a foam composition. The foam composition includes a polylactic acid polymer; a second polymer having a $T_g$ of at least 25° C.; and a plasticizer. The foam composition comprises an open celled foam.

Embodiment 27 is a foam sheet comprising the foam composition of any of embodiments 1 to 26.

Embodiment 28 is a hearing protection article comprising the foam composition of any of embodiments 1 to 26.

Embodiment 29 is the hearing protection article of embodiment 28, wherein the article comprises an earplug.

Embodiment 30 is the hearing protection article of embodiment 28, wherein the article comprises an earmuff.

Embodiment 31 is a method of making a foam composition. The method includes compressing a mixture comprising a polylactic acid polymer; a second polymer having a $T_g$ of at least 25° C.; a plasticizer; and a blowing agent; and heating the compressed mixture, thereby forming the foam composition.

Embodiment 32 is the method of embodiment 31, wherein the mixture further includes a crosslinking agent and a crosslink catalyst.

Embodiment 33 is the method of embodiment 31 or embodiment 32, wherein the crosslink catalyst comprises an alkyl or alkenyl ammonium, phosphonium, or imidizolium salt.

Embodiment 34 is the method of any of embodiments 31 to 33, wherein the crosslink catalyst is of formula (I), (II), (III), or (IV):

$$Q(R^1)_4X \quad (I);$$

$$QR^1(R^2)_3X \quad (II);$$

$$QR^3(R^2)_3X \quad (II);$$

$$Q(R^3)_3R^1X \quad (IV).$$

Wherein Q is nitrogen or phosphorous; $R^1$ is a $C_1$-$C_{20}$ alkyl or alkenyl group; $R^2$ is a $C_1$-$C_8$ alkyl or alkenyl group; $R^3$ is a phenyl group, a benzyl group, or a polycyclic aromatic hydrocarbon group; and X is an anion selected from bromide, iodide, chloride, acetate, sulfate, carbonate, phosphate, tosylate, or hexafluorophosphase.

Embodiment 35 is the method of any of embodiments 31 to 34, wherein the mixture comprises a plurality of pellets.

Embodiment 36 is the method of any of embodiments 31 to 35, wherein the blowing agent includes a chemical blowing agent, a physical blowing agent, or a combination thereof.

Embodiment 37 is the method of any of embodiments 31 to 36, wherein the blowing agent includes a volatile liquid, a gas, a chemical compound, a plurality of expandable microspheres, or a combination thereof.

Embodiment 38 is the method of any of embodiments 31 to 37, wherein the blowing agent includes a plurality of expandable microspheres.

Embodiment 39 is the method of any of embodiments 31 to 38, wherein the blowing agent includes a synthetic azo-based compound, a carbonate-based compound, a hydrazide-based compound, or a combination thereof.

Embodiment 40 is the method of any of embodiments 31 to 38, wherein the blowing agent includes carbon dioxide.

Embodiment 41 is the method of embodiment 40, wherein the carbon dioxide is incorporated into the mixture at a pressure ranging from 300 psi (2.07 MPa) to 10000 psi (68.95 MPa), inclusive.

Embodiment 42 is the method of embodiment 41, wherein the carbon dioxide is incorporated into the mixture by soaking into the mixture for at least 1 minute.

Embodiment 43 is the method of any of embodiments 40 to 42, wherein the second polymer comprises polyvinyl acetate.

Embodiment 44 is the method of any of embodiments 31 to 39, further including blowing the mixture to form a blown foam composition.

Embodiment 45 is the method of any of embodiments 31 to 44, wherein the mixture is compressed in a melt press.

Embodiment 46 is the method of any of embodiments 31 to 45, wherein the compressed mixture is heated in a mold.

Embodiment 47 is the method of any of embodiments 31 to 44, wherein the compressed mixture is heated in an oven.

Embodiment 48 is the method of any of embodiments 31 to 47, wherein the mixture is compressed in an extruder.

Embodiment 49 is the method of any of embodiments 31 to 44 or 48, wherein the compressed mixture is heated in an extruder.

Embodiment 50 is the method of any of embodiments 31 to 49, wherein the compressed mixture is heated at a temperature ranging from 130° C. and 210° C.

Embodiment 51 is a method of making a foam composition. The method includes subjecting a mixture to an elevated pressure; and diffusing a gas into the mixture, followed by ending the subjection to the elevated pressure, thereby forming the foam composition. The mixture includes a polylactic acid polymer; a second polymer having a $T_g$ of at least 25° C.; and a plasticizer.

Embodiment 52 is the method of embodiment 51, wherein the gas is carbon dioxide.

Embodiment 53 is the method of embodiment 51 or 52, wherein the gas is diffused into the mixture in an extruder.

Embodiment 54 is the method of any of embodiments 51 to 53, further including heating the mixture.

Embodiment 55 is the method of any of embodiments 51 to 54, wherein the mixture further includes a physical blowing agent.

Embodiment 56 is the method of any of embodiments 51 to 55, wherein the elevated pressure ranges from 300 psi (2.07 MPa) to 10000 psi (68.95 MPa), inclusive.

Embodiment 57 is the method of embodiment 56, wherein the gas is diffused into the mixture by soaking into the mixture for at least 1 minute.

Embodiment 58 is the method of any of embodiments 51 to 57, wherein the second polymer comprises polyvinyl acetate.

Embodiment 59 is a process. The process includes providing at least one hearing protection article of embodiment 28; and interposing the hearing protection article between an acoustic source and an acoustic receiver in the form of a human ear.

Embodiment 60 is the process of embodiment 59, wherein the hearing protection article provides a transmission loss that is greater than or equal to 10 dB across the range of 0.1 k Hz to 10 kHz and has all dimensions less than or equal to 20 cm in size.

Embodiment 61 is the process of embodiment 59, wherein the hearing protection article is used as an acoustic absorber.

Embodiment 62 is the process of embodiment 59, wherein the hearing protection article further includes at least one casing that at least partially encloses the hearing protection article and is adapted for contact with the human ear.

The following Examples are set forth to describe additional features and embodiments of the invention. All parts are by weight unless otherwise indicated.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims. Unless otherwise noted, amounts of material are listed by weight, or by weight percent ("wt-%").

Materials

INGEO 4032D—a semicrystalline polylactic acid (PLA) (2 wt.-% D-lactide; weight average molecular weight≈200,000 g/mol), was purchased from Natureworks, LLC.

INGEO 4060—an amorphous polylactic acid (PLA), was purchased from Natureworks, LLC.

VINAVIL K70—a polyvinyl acetate (PVAc) ($T_g$=42° C.; weight average molecular weight 400,000 g/mol), was obtained from Vinavil, Italy.

VINNAPAS UW 4 FS—a polyvinyl acetate ($T_g$=42° C.; weight average molecular weight 280,000 g/mol), was obtained from Wacker, Germany.

CITROFLEX A4—acetyl tributyl citrate, a plasticizer, was obtained from Vertellus Performance Materials, Bayonne, N.J.

ECOPROMOTE—zinc phenylphosphonate, a crystallization nucleation agent, was obtained from Nissan Chemical Industrials (Japan).

SUKANO S511—slip/antiblock additive in PLA masterbatch, was obtained from Sukano.

PETROTHENE NA217000—a low density polyethylene (LDPE) was purchased from LyondellBasell Industries, Houston, Tex.

1,1'-AZODICARBAMIDE (AZO)—chemical blowing agent, was obtained from Sigma-Aldrich.

JONCRYL ADR 4368 (J4368)—crosslinking agent, was obtained from BASF.

DODECYLTRIMETHYLAMMONIUM BROMIDE (DMTAB)—crosslinking catalyst, was obtained from TCI chemicals.

TETRAOCTYLAMMONIUM BROMIDE (TOAB)—crosslinking catalyst, was obtained from Alfa Aesar.

TETRABUTYL AMMONIUM IODIDE (TBAI)—crosslinking catalyst, was obtained from Sigma-Aldrich.

TETRAOCTADECYL AMMONIUM BROMIDE (TODAB)—crosslinking catalyst, was obtained from Sigma-Aldrich.

TETRABUTYL AMMONIUM BROMIDE (TBAB)—crosslinking catalyst, was obtained from Alfa Aesar.

BENZYL TRIETHYLAMMONIUM CHLORIDE (BTEAC)—crosslinking catalyst, was obtained from Alfa Aesar.

TETRABUTYL AMMONIUM CHLORIDE (TBAC)—crosslinking catalyst, was obtained from Fluka.

TETRABUTYL PHOSPHONIUM BROMIDE (MTPPB)—crosslinking catalyst, was obtained from Alfa Aesar.

METHYL TRIPHENYL PHOSPHONIUM BROMIDE (MTPPB)—crosslinking catalyst, was obtained from Sigma-Aldrich.

METHYL TRIPHENYL PHOSPHONIUM CHLORIDE (MTPPC)—crosslinking catalyst, was obtained from Sigma-Aldrich.

EXPANCEL 930 MB 120—physical blowing agent, was obtained from Akzo Nobel.

EXPANCEL 950 MB 80—physical blowing agent, was obtained from Akzo Nobel.

TALC—magnesium silicate monohydrate, a cell nucleating agent, was obtained from Alfa Aesar.

ISOOCTYLTRIMETHOXYSILANE—surface functionalizer (obtained from Gelest, Tullytown, Pa.).

METHYLTRIMETHOXYSILANE—surface functionalizer (obtained from Gelest, Tullytown, Pa.).

NALCO 2326—16 wt. % colloidal silica (obtained from Nalco Co., Naperville, Ill.).

SILQUEST A1230—nonionic PEG silane surface functionalizer (obtained from Momentive, Friendly, W. Va.).

CG-2—5 nm silica functionalized with octyl silane, was made according to Preparative Example 3 (PE-3).

PEG-FUNCTIONALIZED SILICA NANOPARTICLES, was made according to Preparative Example 4 (PE-4).

DAY GLO MP-PR5547—coloring agent, was obtained from Day Glo Color Corp (Cleveland, Ohio).

HALLGREEN R-8010 (HG R8010)—an oligomeric polyester plasticizer (average molecular weight 5,000 g/mol), was obtained from The HallStar Company (Chicago, Ill.).

HALLGREEN R-8040 (HG R8040)—an oligomeric polyester plasticizer (average molecular weight 3,000 g/mol), was obtained from Hallstar (Chicago, Ill.).

SPHERIGLASS 5000-A (glass beads)—solid glass bead (7-10 μm), a cell nucleating agent, was obtained from Potters Industries, Inc (Malvern, Pa.).

POLYSTYRENE PARTICLES (PS beads)—solid polystyrene bead (4 μm), a cell nucleating agent, was obtained from Sekisui Plastics (Tokyo, Japan).

POLYVINYL PYROLLIDONE K30 (PVP)—was obtained from TCI America (Portland, Oreg.)

LYCOAT RS780 (starch)—hydroxypropyl starch was obtained from Roquette Freres (Lestrem, France).

Sample Preparation

Melt Compounding

Samples were prepared by mixing PLA, PVAc, plasticizer and nucleation agent in a DSM XPLORE 15 cm³ twin-screw micro-compounder at 100 RPM, 200° C. for 10 minutes, and then collecting the sample by opening a valve on the mixing chamber. The compounded samples were subjected to aging testing at 80° C. and DSC characterization.

Crosslinking of Flexible PLA Blends

The effect of crosslinking agent and crosslinking catalyst on the melt viscosity of the flexible PLA blends was assessed by mixing pre-compounded plasticized PLA/PVAc pellets with crosslinking agent and/or crosslinking catalyst in a twin screw extruder. The torque of the screws were monitored over time to assess crosslinking, using a WinMix Brabender Mixing Program, version 4.2.5.

Preparation of Polymer Prefoam Resins

Polymer resins were compounded on a Brabender twin-screw mixer at 110° C. and 100 RPM by mixing pre-compounded plasticized PLA/PVAc pellets with additional CITROFLEX A4 and/or crosslinking agent and/or chemical blowing agent and/or crosslinking catalyst and/or color and/or crystallization nucleating agents and/or cell nucleating agents and/or slip/antiblock additives and/or cell stabilizers.

Preparation of Polymer Prefoam Sheets

Compounded prefoam resins were pressed between two aluminum sheets with polytetrafluoroethylene liners and 1-3 85 micrometer shims. The Carver press was set to 265° F. (129° C.). The resin was allowed to soften for 3 minutes and then pressed at 6 metric tons for 1 minute.

Foaming in a Mold

A section of melt-pressed polymer sheet was inserted into a cylindrical aluminum mold with dimensions of 0.75 inch (1.9 cm) deep and 0.5 inch (1.3 cm) wide. The mold was heated at 190° C. in a heating press for 10 minutes, then immediately cooled to room temperature using a cooling press.

Foaming in an Oven when Using Strip Shaped Samples

A 1 inch (2.5 cm) by 2.5 inch (6.4 cm) by 0.04 inch (0.1 cm) cutout of melt-pressed polymer was place on a strip of aluminum foil coated with mold release and placed in an oven set at 190° C. Samples were allowed to foam between 0-15 min.

Foaming in Oven when Using Disk Shaped Samples

A 0.7 inch (1.78 cm) by 0.04 inch (0.1 cm) disk of melt-pressed polymer resin was placed on a Teflon liner and placed in an oven at either 210, 230, or 250° C. Samples were allowed to foam between 0-15 min.

Foaming in a Pressure Vessel 35 mm×25 mm rectangles were cut from the melt-pressed polymer resins and placed in a 725 mL steel pressure vessel obtained from John C. Ernst (Sparta, N.J.). The vessel was pressurized with $CO_2$ and heated to various temperatures. The resin was soaked in the pressure vessel for a period of time at which point the pressure was released from the chamber, leading to foam. The foam was allowed to equilibrate at room temperature for 24 hours.

Test Methods

Aging Test

The compounded samples (about 0.2 grams) were placed in the closed scintillation vials to prevent plasticizer evaporation during aging testing, and aged in the oven at 80° C. for 24 hours. Then, after aging at 80° C., the sample's surface was inspected to see if there was plasticizer migration. Samples having an oily surface were considered to fail; whereas samples having a non-oily surface were considered to pass.

DSC—Differential Scanning Calorimetry

The glass transition temperature and melting peak temperature of each sample was measured using a TA INSTRUMENTS DIFFERENTIAL SCANNING CALORIMETER according to ASTM D3418-12 unless specified otherwise. Each sample (4-8 mg) was heated from −60° C. to 200° C. at 10° C./min in a first heating scan and held for 2 minutes to erase its thermal history, then cooled to −60° C. at 5° C./min in a first cooling scan, and heated to 200° C. at 10° C./min in a second heating scan. The second heating scan was used to determine $T_g$ and $T_m$ of the samples. Various parameters were derived from the DSC as defined as follows:

$T_g$—refers to the midpoint temperature of the second heating scan, described as $T_{mg}$ in ASTM D3418-12.

$T_m$—refer to the melting peak temperature of the second heating scan, described as $T_{pm}$ in ASTM D3418-12.

Scanning Electron Microscropy (SEM)

The cell structure of the flexible PLA foams was determined by SEM using a Jeol JSM-6010LA SEM. Samples were prepared by mounting a slice along the cylindrical axis of the molded PLA foam on a Jeol SEM stage and sputter coating with Au/Pd for 30 seconds in a Denton Vacuum Desk V. The images were analyzed using Image Pro-Premier 9.1 Image analysis software to obtain average cell diameter, average cell area, average cell roundness, and cells/cm².

cell homogeneity=$1/\sigma_{cell\ diameter}$ roundness=longest cross-section of cell/shortest cross-section of cell Density Measurement A pycnometer was used to measure the density of the foamed PLA/PVAc structure. The buoyancy force was measured according to ASTM D3575-13 Suffix AA-Buoyancy (also called Specific Buoyancy). The density was then calculated using Archimedes' principal. The density was calculated by measuring the mass of the foamed sample in dry air and the buoyant force of the sample in water.

$$\rho_{foam} = \frac{m_{dry}}{m_{dry} - m_{buoyant}}$$

The wt.-% of each of the components utilized in the compositions of the examples and control examples (indicated by the "C") is given in Table 1. For example, Example 5 contained 70 wt.-% of PLA4032, 15 wt.-% of VinnapasUW4 (PVAc), and 15 wt.-% of CITROFLEX A4, based on the total weight of polylactic acid polymer, polyvinyl acetate polymer, and plasticizer. Example 5 further contained 0.2 wt.-% of ECOPROMOTE based on the total weight of the composition. The $T_g$, $T_m$ and aging results of the compositions are also reported in Table 1 as follows:

TABLE 1

| Example | Components | Wt.-% of component | $T_g$ (° C.) | $T_m$ (° C.) | Aging at 80° C. for 24 hrs |
|---|---|---|---|---|---|
| C1 | PLA4032/CITROFLEX A4/ECOPROMOTE | 90/10/0.2 | 32 | 162 | Pass |
| C2 | PLA4032/CITROFLEX A4/ECOPROMOTE | 86/14/0.2 | 25 | 160 | Pass |
| C3 | PLA4032/CITROFLEX A4/ECOPROMOTE | 85/15/0.2 | 21 | 158 | Fail |
| C4 | PLA4032/CITROFLEX A4/ECOPROMOTE | 83/17/0.2 | 15 | 164 | Fail |
| 5 | PLA4032/VINNAPSUW4/CITROFLEX A4/ECOPROMOTE | 70/15/15/0.2 | 15 | 165 | Pass |
| 6 | PLA4032/VINNAPASUW4/CITROFLEX A4/ECOPROMOTE | 67/16/16/1 | 10 | 163 | Pass |
| 7 | PLA4032/VINNAPASUW4/CITROFLEX A4/ECOPROMOTE | 65/20/15/0.2 | 17 | 165 | Pass |
| 8 | PLA4032/VINNAPASUW4/CITROFLEX A4/ECOPROMOTE | 60/25/15/0.2 | 11 | 164 | Pass |
| 9 | PLA4032/VINNAPASUW4/CITROFLEX A4/ECOPROMOTE | 50/35/15/0.1 | 5 | 160 | Pass |
| 10 | PLA4032/VINNAPASUW4/CITROFLEX A4/ECOPROMOTE | 45/35/20/0.2 | 2 | 160 | Pass |
| 11 | PLA4060/PLA4032/VINAVILK70/CITROFLEX A4/ECOPROMOTE | 20/20/35/25/0.2 | 3 | 156 | Pass |
| 12 | PLA4060/PLA4032/VINAVILK70/CITROFLEX A4/ECOPROMOTE | 10/30/35/25/0.2 | 0 | 154 | Pass |

As illustrated by Table 1, Comparative Examples $C_1$ and $C_2$ passed the aging test, yet Comparative Examples $C_3$ and $C_4$ failed the aging test. The $T_g$ of the sample can be lowered to 25° C. (as illustrated by Comparative C$_2$), but not below 25° C. yet still pass the aging test (as illustrated by Comparative Examples C$_3$ and C$_4$). When the composition included PLA, plasticizer and PVAc, the T$_g$ can be reduced below 25° C. and pass the aging test.

Example 13 (EX-13)

A twin screw extruder (Zone 1: 250° F. (121° C.); Zones 2 and 3: 390° F. (199° C.); Zones 4 and 5: 350° F. (177° C.)) and underwater pelletizer were used to prepare pre-compounded and free-flowing PLA pellets, which had the following composition:

| Components | Composition (wt.-%) |
|---|---|
| INGEO 4032 PLA | 62.6 |
| VINAVIL K70 PVAc | 21 |
| CITROFLEX A4 Plasticizer | 16 |
| ECOPROMOTE Crystallization Nucleating Agent | 0.4 |

92 wt.-% pre-compounded PLA pellets and 8 wt.-% EXPANCEL 950 MB 80 were dry-blended together and fed to single-screw extruders. A seven layer blown film line was used, with each layer fed by a 20 mm single screw extruder. The extruders were operated at the following approximate zone and die temperatures: Z1: 185° C. (365° F.); Z2: 185° C. (365° F.); Z3: 185° C. (365° F.); Z4: 185° C. (365° F.); and 185° C. (365° F.). The outer and inner two layers consisted of LDPE with the thickness of each layer approximately 0.001 inch (0.025 mm), and the middle three layers consisted of plasticized PLA/PVAc foams with a total thickness of about 0.017 mil (0.425 mm). After the blown film/foam extrusion, the LDPE films were easily separated from the plasticized PLA/PVAc foam. The PLA foam sample was examined by an optical microscope: the expandable microspheres formed closed cells with relatively uniform sizes, having diameters in the range of 100~250 micrometers. The density of the foam sample was measured to be 0.31 gram/cm$^3$, which was 74% less than the density of the plasticized PLA/PVAc blends with a density of 1.20 gram/cm$^3$.

Preparative Example 1 (PE-1)

A twin screw extruder from APV Chemical Machinery (Saginaw, Mich.) (screw diameter: 30 mm; ratio of screw length to diameter: 30; extrusion throughput rate: 20 pounds per hour (9 kilograms/hour); Zone 1: 250° F. (121° C.); Zones 2 and 3: 390° F. (199° C.); Zones 4 and 5: 350° F. (177° C.)) and an underwater pelletizer from Gala Industries (Eagle Rock, Va.) were used to prepare pre-compounded and free-flowing PLA pellets, which had the following composition:

| Components | Composition (wt.-%) |
|---|---|
| INGEO 4060 PLA | 30 |
| INGEO 4032 PLA | 7.8 |
| VINAVIL K70 PVAc | 35 |
| CITROFLEX A4 Plasticizer | 25 |
| ECOPROMOTE Crystallization Nucleating Agent | 0.2 |
| SUKANO DC S511 Slip/Antiblock Masterbatch | 2 |

The PE-1 pre-compounded PLA pellets were used as the base resin to prepare foam samples as described below.

Preparative Example 2 (PE-2)

A twin screw extruder (Zone 1: 250° F. or 121° C.; Zones 2 and 3: 390° F. or 199° C.; Zones 4 and 5: 350° F. or 177° C.) and underwater pelletizer were used to prepare pre-compounded and free-flowing PLA pellets, which had the following composition:

| Components | Composition (wt.-%) |
|---|---|
| INGEO 4060 PLA | 20 |
| INGEO 4032 PLA | 17.8 |
| VINAVIL K70 PVAc | 35 |
| CITROFLEX A4 Plasticizer | 25 |
| ECOPROMOTE Crystallization Nucleating Agent | 0.2 |
| SUKANO DC S511 Slip/Antiblock Masterbatch | 2 |

Preparative Example 3 (PE-3)

CG-2 hydrophobic functionalized silica nanoparticles were prepared as follows: 7.65 g isooctyltrimethoxysilane, 0.79 g methyltrimethoxysilane, 90 g ethanol, 23 g of methanol and 100 g of NALCO 2326 (16 wt. % solids) were combined in a three-neck flask equipped with a water cooled condenser and a mechanical stirrer. The mixture was stirred at 80° C. overnight. The mixture was then dried in a flow through oven at 150° C. to produce the surface-modified nanoparticles as a white particulate solid.

Preparative Example 4 (PE-4)

PEG-functionalized hydrophilic silica nanoparticles were prepared as follows: 9.92 SILQUEST A1230 and 100 g of NALCO 2326 (16 wt. % solids) colloidal silica were combined in a three-neck flask equipped with a water-cooled condenser and a mechanical stirrer. The mixture was stirred at 50° C. overnight. The mixture was allowed to air dry for 24 hours to produce the surface-modified nanoparticles as a particulate solid.

Example 14 (EX-14)

A 1.0 g sample of polymer prefoam resin (EX-14) composed of 89.2 parts pre-compounded PLA pellets (PE-1), 4.4 parts CITROFLEX A4, 0.2 parts J4368, 0.2 parts DTMAB, 5 parts AZO, 1 part color was foamed in a mold.

Example 15 (EX-15)

A 1.0 g sample of polymer prefoam resin (EX-15) composed of 89.0 parts pre-compounded PLA pellets (PE-1), 4.4 parts CITROFLEX A4, 0.4 parts J4368, 0.2 parts DTMAB, 5 parts AZO, 1 part color was foamed in a mold.

Example 16 (EX-16)

A 1.0 g sample of polymer prefoam resin (EX-16) composed of 89.0 parts pre-compounded PLA pellets (PE-1), 4.4 parts CITROFLEX A4, 0.4 parts J4368, 0.2 parts TOAB, 5 parts AZO, 1 part color was foamed in a mold.

Example 17 (EX-17)

A 1.0 g sample of polymer prefoam resin (EX-17) composed of 93.4 parts pre-compounded PLA pellets (PE-1), 0.4 parts J4368, 0.2 parts TBAI, 5 parts AZO, 1 part color was foamed in a mold.

Example 18 (EX-18)

A 1.0 g sample of polymer prefoam resin (EX-18) composed of 91.4 parts pre-compounded PLA pellets (PE-1), 0.4 parts J4368, 0.2 parts TBAI, 5 parts AZO, 1 part color, 2 parts talc was foamed in a mold.

Example 19 (EX-19)

A 1.0 g sample of polymer prefoam resin (EX-19) composed of 88.4 parts pre-compounded PLA pellets (PE-1), 0.4 parts J4368, 0.2 parts TBAI, 5 parts AZO, 1 part color, 5 parts talc was foamed in a mold.

Example 20 (EX-20)

A 1.0 g sample of polymer prefoam resin (EX-20) composed of 83.4 parts pre-compounded PLA pellets (PE-1), 0.4 parts J4368, 0.2 parts TBAI, 5 parts AZO, 1 part color, 10 parts talc was foamed in a mold.

Example 21 (EX-21)

A 1.0 g sample of polymer prefoam resin (EX-21) composed of 83.6 parts pre-compounded PLA pellets (PE-1), 0.2 parts J4368, 0.2 parts DTMAB, 5 parts AZO, 1 part color, 10 parts talc was foamed in a mold.

Example 22 (EX-22)

A 1.0 g sample of polymer prefoam resin (EX-22) composed of 83.6 parts pre-compounded PLA pellets (PE-1), 0.2 parts J4368, 0.2 parts DTMAB, 5 parts AZO, 1 part color, 10 parts $TiO_2$ was foamed in a mold.

Example 23 (EX-23)

A 1.0 g sample of polymer prefoam resin (EX-23) composed of 91.6 parts pre-compounded PLA pellets (PE-1), 0.2 parts J4368, 0.2 parts DTMAB, 5 parts AZO, 1 part color, 2 parts CG-2 was foamed in a mold.

Example 24 (EX-24)

A 1.0 g sample of polymer prefoam resin (EX-24) composed of 88.6 parts pre-compounded PLA pellets (PE-1), 0.2 parts J4368, 0.2 parts DTMAB, 5 parts AZO, 1 part color, 5 parts CG-2 was foamed in a mold.

Example 25 (EX-25)

A 1.0 g sample of polymer prefoam resin (EX-25) composed of 83.6 parts pre-compounded PLA pellets (PE-1), 0.2 parts J4368, 0.2 parts DTMAB, 5 parts AZO, 1 part color, 10 parts CG-2 was foamed in a mold.

Comparative Example 5 (C-5)

A 1.0 g sample of polymer resin (C-5) composed of 94.3 parts pre-compounded PLA pellets (PE-2), 4.7 parts AZO, 1 part color was foamed in a mold.

Comparative Example 6 (C-6)

A 1.0 g sample of polymer resin (C-6) composed of 94.3 parts pre-compounded PLA pellets (PE-1), 4.7 parts AZO, 1 part color was foamed in a mold.

Comparative Example 7 (C-7)

A 1.0 g sample of polymer resin (C-7) composed of 99 parts pre-compounded PLA pellets (PE-1), 1 part color was foamed in a mold.

Comparative Example 8 (C-8)

A 1.0 g sample of polymer resin (C-8) composed of 94.3 parts pre-compounded PLA pellets (PE-1), 4.3 parts AZO, 0.4 parts J4368, 1 part color was foamed in a mold.

Table 2 summarizes the characterization of foams of plasticized PLA blends foamed in a confined mold for 10 minutes at 190° C.

TABLE 2

Characterization of foams from EX-14 to EX-25 and C-5 to C-8.

| Foam | Cell diameter (mm) | Cell homogeneity | Cell area (mm$^2$) | Cell roundness | Cell density (cell/cm$^2$) |
|---|---|---|---|---|---|
| EX-14 | 0.490 | 2.51 | 0.325 | 1.163 | 167 |
| EX-15 | 0.417 | 4.39 | 0.184 | 1.178 | 298 |
| EX-16 | 0.519 | 3.76 | 0.280 | 1.246 | 187 |
| EX-17 | 0.702 | 3.42 | 0.47 | 1.287 | 127 |
| EX-18 | 0.628 | 3.33 | 0.393 | 1.306 | 257 |
| EX-19 | 0.469 | 4.27 | 0.227 | 1.369 | 329 |
| EX-20 | 0.395 | 6.06 | 0.15 | 1.295 | 392 |
| EX-21 | 0.475 | 6.21 | 0.202 | 1.128 | 346 |
| EX-22 | 0.405 | 2.81 | 0.239 | 1.141 | 202 |
| EX-23 | 0.42 | 5.18 | 0.172 | 1.134 | 355 |
| EX-24 | 0.37 | 3.61 | 0.171 | 1.129 | 294 |
| EX-25 | 0.432 | 2.82 | 0.252 | 1.163 | 218 |
| C-5 | Did not fill mold | | | | |
| C-6 | Did not fill mold | | | | |
| C-7 | Did not fill mold | | | | |
| C-8 | Did not fill mold | | | | |

Example 26 (EX-26)

A 1.0 g sample of polymer prefoam resin (EX-26) composed of 91.4 parts pre-compounded PLA pellets (PE-1), 0.4 parts J4368, 0.2 parts DTMAB, 5 parts AZO, 1 part color and 2 parts EXPANCEL was cut into strips and foamed in an oven at 190° C.

Example 27 (EX-27)

A 1.0 g sample of polymer prefoam resin (EX-27) composed of 91.6 parts pre-compounded PLA pellets (PE-1), 0.4 parts J4368, 5 parts AZO, 1 part color and 2 parts EXPANCEL was cut into strips and foamed in an oven at 190° C.

Table 3 summarizes the characterization of EX-26 and EX-27 foamed in an oven at 190° C. for various times.

TABLE 3

Characterization of foams from EX-26 and EX-27.

| Foam | Foaming time | Foam height (mm) | Cell diameter (mm) | Cell homogeneity | Cell area (mm$^2$) |
|---|---|---|---|---|---|
| EX-26 | 0 min | 0.93 | n/a | n/a | n/a |
| | 4 min | 1.59 | 0.152 | 1.12 | 0.026 |
| | 6 min | 2.23 | 0.271 | 6.99 | 0.077 |
| | 8 min | 3.22 | 0.414 | 3.64 | 0.202 |
| | 10 min | 4.08 | 0.606 | 2.08 | 0.49 |
| | 15 min | 2.68 | 0.378 | 3.37 | 0.192 |
| EX-27 | 10 min | 1.25 | 0.151 | 8.00 | 0.031 |

Example 28 (EX-28)

A 35 mm×25 mm×2 mm sample of polymer resin (EX-28) composed of 99.7 parts pre-compounded PLA pellets (PE-1), 0.1 parts J4368, 0.2 parts TBAI was foamed in a pressure vessel using a 1 hour soak time at 700 PSI (~4.8 MPa) and 70° C. The pressure was released over 12 minutes.

Example 29 (EX-29)

A 35 mm×25 mm×2 mm sample of polymer resin (EX-29) composed of 99.65 parts pre-compounded PLA pellets (PE-1), 0.15 parts J4368, 0.2 parts TBAI was foamed in a pressure vessel using a 1 hour soak time at 700 PSI (~4.8 MPa) and 70° C. The pressure was released over 12 minutes.

Example 30 (EX-30)

A 35 mm×25 mm×2 mm sample of polymer resin (EX-30) composed of 99.6 parts pre-compounded PLA pellets (PE-1), 0.2 parts J4368, 0.2 parts TBAI was foamed in a pressure vessel using a 1 hour soak time at 700 PSI (~4.8 MPa) and 70° C. The pressure was released over 12 minutes.

Example 31 (EX-31)

A 35 mm×25 mm×2 mm sample of polymer resin (EX-31) composed of 99.2 parts pre-compounded PLA pellets (PE-1), 0.6 parts J4368, 0.2 parts TBAI was foamed in a pressure vessel using a 1 hour soak time at 700 PSI (~4.8 MPa) and 70° C. The pressure was released over 12 minutes.

Example 32 (EX-32)

A 35 mm×25 mm×2 mm sample of polymer resin (EX-32) composed of 98.0 parts pre-compounded PLA pellets (PE-1), 1.8 parts J4368, 0.2 parts TBAI was foamed in a pressure vessel using a 1 hour soak time at 700 PSI (~4.8 MPa) and 70° C. The pressure was released over 12 minutes.

Example 33 (EX-33)

A 35 mm×25 mm×2 mm sample of polymer resin (EX-33) composed of 99.7 parts pre-compounded PLA pellets (PE-1), 0.1 parts J4368, 0.2 parts TBAI was foamed in a pressure vessel using a 0.5 hour soak time at 700 PSI (~4.8 MPa) and 70° C. The pressure was released over 11 minutes.

Example 34 (EX-34)

A 35 mm×25 mm×2 mm sample of polymer resin (EX-34) composed of 99.7 parts pre-compounded PLA pellets (PE-1), 0.1 parts J4368, 0.2 parts TBAI was foamed in a pressure vessel using a 0.25 hour soak time at 700 PSI (~4.8 MPa) and 70° C. The pressure was released over 10 minutes.

Example 35 (EX-35)

A 35 mm×25 mm×2 mm sample of polymer resin (EX-35) composed of 99.7 parts pre-compounded PLA pellets (PE-1), 0.1 parts J4368, 0.2 parts TBAI was foamed in a pressure vessel using a 1 hour soak time at 700 PSI (~4.8 MPa) and 50° C. The pressure was released over 10 minutes.

Example 36 (EX-36)

A 35 mm×25 mm×2 mm sample of polymer resin (EX-36) composed of 99.7 parts pre-compounded PLA pellets (PE-1), 0.1 parts J4368, 0.2 parts TBAI was foamed in a pressure vessel using a 1 hour soak time at 700 PSI (~4.8 MPa) and 90° C. The pressure was released over 11 minutes.

Example 37 (EX-37)

A 35 mm×25 mm×2 mm sample of polymer resin (EX-37) composed of 99.7 parts pre-compounded PLA pellets (PE-1), 0.1 parts J4368, 0.2 parts TBAI was foamed in a pressure vessel using a 1 hour soak time at 900 PSI (~6.2 MPa) and 70° C. The pressure was released over 11 minutes.

Example 38 (EX-38)

A 35 mm×25 mm×2 mm sample of polymer resin (EX-38) composed of 99.8 parts pre-compounded PLA pellets (PE-1), 0.2 parts TBAI was foamed in a pressure vessel using a 1 hour soak time at 700 PSI (~4.8 MPa) and 70° C. The pressure was released over 12 minutes.

Table 4 summarizes the characterization of flexible PLA blends foamed using a $CO_2$ pressure vessel.

TABLE 4

Characterization of foams EX-28-EX-38.

| Foam | Cell diameter, micrometers | Cell homogeneity | Cell area, $mm^2$ | Cell roundness | Cell density, cell/$mm^2$ |
|---|---|---|---|---|---|
| EX-28 | 83 | 37.0 | 0.325 | 1.163 | 11100 |
| EX-29 | 70 | 30.3 | 0.184 | 1.178 | 13200 |
| EX-30 | 56 | 37.0 | 0.280 | 1.246 | 22000 |
| EX-31 | 65 | 30.3 | 0.47 | 1.287 | 15500 |
| EX-32 | 91 | 22.7 | 0.393 | 1.306 | 9950 |
| EX-33 | 68 | 32.3 | 0.227 | 1.369 | 12400 |
| EX-34 | 110 | 13.9 | 0.15 | 1.295 | 5690 |
| EX-35 | 90 | 24.4 | 0.202 | 1.128 | 13800 |
| EX-36 | 155 | 17.5 | 0.239 | 1.141 | 2350 |
| EX-37 | 237 | 8.8 | 0.172 | 1.134 | 1660 |
| EX-38 | Did not change dimensions | | | | |

Example 39 (EX-39)

Figure 5:
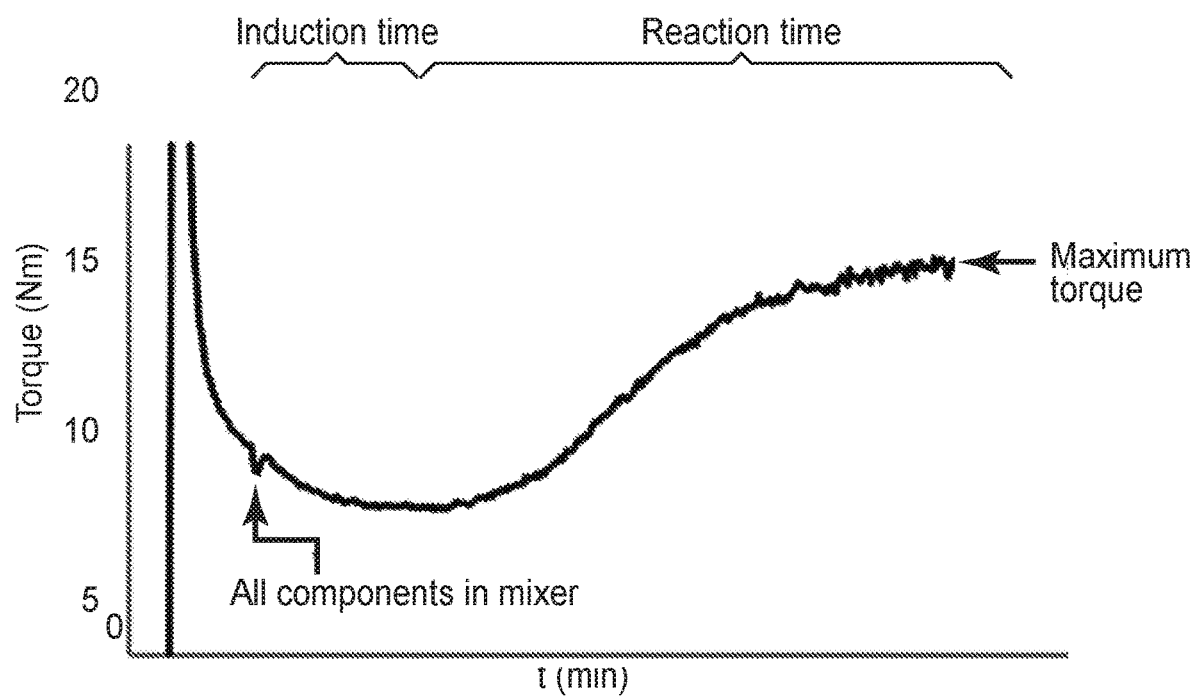
FIG. 5 is a plastogram of the mixed components of Example 39.
Figure 6:
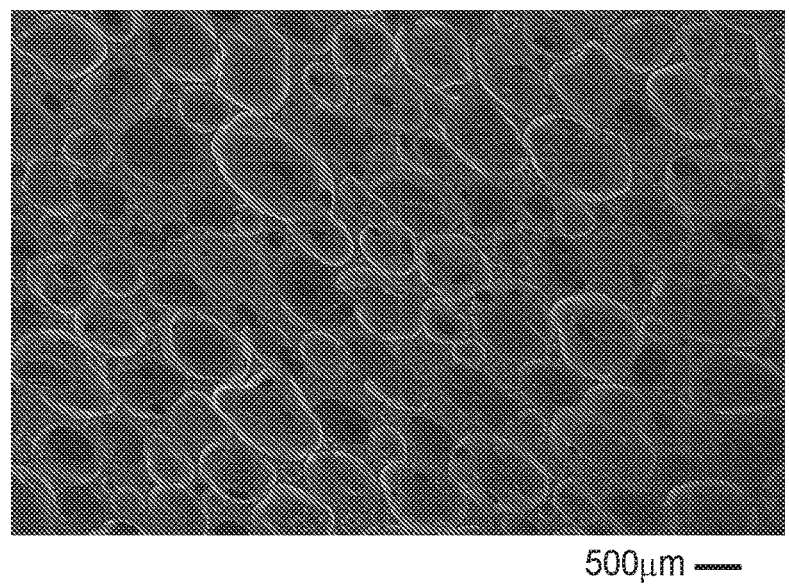
FIG. 6 is an SEM image of the foam composition of Example 57.

A mixture of 99.2 parts pre-compounded PLA pellets (PE-1), 0.6 parts J4368, 0.2 parts DTMAB was compounded in a twin-screw mixer at 110° C. The torque of the screws was monitored for 14 minutes. FIG. 5 is a plastogram of EX-39 after all components (i.e., the PLA pellets, J4368, and DTMAB) were added to the mixer. The induction time, reaction time, and maximum torque are illustrated.

Example 40 (EX-40)

A mixture of 99.2 parts pre-compounded PLA pellets (PE-1), 0.6 parts J4368, 0.2 parts TBAB was compounded in a twin-screw mixer at 110° C. The torque of the screws was monitored for 14 minutes.

Example 41 (EX-41)

A mixture of 99.2 parts pre-compounded PLA pellets (PE-1), 0.6 parts J4368, 0.2 parts TBAI was compounded in a twin-screw mixer at 110° C. The torque of the screws was monitored for 14 minutes.

Example 42 (EX-42)

A mixture of 99.2 parts pre-compounded PLA pellets (PE-1), 0.6 parts J4368, 0.2 parts TOAB was compounded in a twin-screw mixer at 110° C. The torque of the screws was monitored for 14 minutes.

Example 43 (EX-43)

A mixture of 99.2 parts pre-compounded PLA pellets (PE-1), 0.6 parts J4368, 0.2 parts TBAC was compounded in a twin-screw mixer at 110° C. The torque of the screws was monitored for 14 minutes.

Example 44 (EX-44)

A mixture of 99.2 parts pre-compounded PLA pellets (PE-1), 0.6 parts J4368, 0.2 parts BTEAC was compounded in a twin-screw mixer at 110° C. The torque of the screws was monitored for 14 minutes.

Example 45 (EX-45)

A mixture of 99.2 parts pre-compounded PLA pellets (PE-1), 0.6 parts J4368, 0.2 parts TODAB was compounded in a twin-screw mixer at 110° C. The torque of the screws was monitored for 14 minutes.

Example 46 (EX-46)

A mixture of 99.2 parts pre-compounded PLA pellets (PE-1), 0.4 parts J4368, 0.4 parts TBPB was compounded in a twin-screw mixer at 110° C. The torque of the screws was monitored for 14 minutes.

Example 47 (EX-47)

A mixture of 99.2 parts pre-compounded PLA pellets (PE-1), 0.4 parts J4368, 0.4 parts MTTPB was compounded in a twin-screw mixer at 110° C. The torque of the screws was monitored for 14 minutes.

Example 48 (EX-48)

A mixture of 99.2 parts pre-compounded PLA pellets (PE-1), 0.4 parts J4368, 0.4 parts MTTPC was compounded in a twin-screw mixer at 110° C. The torque of the screws was monitored for 14 minutes.

Example 49 (EX-49)

A mixture of 99.4 parts pre-compounded PLA pellets (PE-1) and 0.6 parts J4368 was compounded in a twin-screw mixer at 190° C. The torque of the screws was monitored for 30 minutes.

Example 50 (EX-50)

A mixture of 99.2 parts pre-compounded PLA pellets (PE-1), 0.6 parts J4368, 0.2 parts DTMAB was compounded in a twin-screw mixer at 190° C. The torque of the screws was monitored for 30 minutes.

Comparative Example 9 (C-9)

Pre-compounded PLA pellets (PE-1) were added to a twin-screw mixer at 110° C. The torque of the screws was monitored for 15 minutes.

Comparative Example 10 (C-10)

A mixture of 99.4 parts pre-compounded PLA pellets (PE-1) and 0.6 parts J4368 was compounded in a twin-screw mixer at 110° C. The torque of the screws was monitored for 15 minutes.

Comparative Example 11 (C-11)

Pre-compounded PLA pellets (PE-1) were added to a twin-screw mixer at 110° C. The torque of the screws was monitored for 30 minutes.

Table 5 summarizes the impact of crosslink catalyst structure on the reaction between flexible PLA blends and J4368 at 110° C.

TABLE 5

Effect of crosslinking catalyst structure on the reaction between flexible PLA blends and J4368 at 110° C.

| Sample | Induction time (min) | Reaction time (min) | Maximum torque (Nm) |
|---|---|---|---|
| C-9 | no reaction in 15 min | | 7.4 |
| C-10 | no reaction in 15 min | | 7.4 |
| EX-39 | 3 | 7 | 16.1 |
| EX-40 | 0.25 | 7 | 17.5 |
| EX-41 | 0.25 | 4 | 15.3 |
| EX-42 | 1.25 | 6 | 14.7 |
| EX-43 | 1.75 | 5 | 9.9 |
| EX-44 | >12 | n.d. | 9.0 |
| EX-45 | 3 | >10 | 9.0 |
| EX-46 | 0.25 | 3 | 15.4 |
| EX-47 | 2.25 | 7 | 16.1 |
| EX-48 | 3.25 | 8 | 12.6 |

Table 6 summarizes the impact of crosslinking catalyst on the reaction between flexible PLA blends and J4368 at 190° C.

TABLE 6

Effect of crosslinking catalyst on the reaction between flexible PLA blends and J4368 at 190° C.

| Sample | Induction time (min) | Reaction time (min) | Maximum torque (Nm) |
|---|---|---|---|
| C-11 | no reaction in 15 min | | 0.8 |
| EX-49 | 0 | 21 | 2.8 |
| EX-50 | 0 | 6 | 2.3 |

Example 51 (EX-51)

A mixture of 99.5 parts pre-compounded PLA pellets (PE-1), 0.4 parts J4368, 0.1 parts TBAI was compounded in a twin-screw mixer at 110° C. The torque of the screws was monitored for 10 minutes.

Example 52 (EX-52)

A mixture of 99.4 parts pre-compounded PLA pellets (PE-1), 0.4 parts J4368, 0.2 parts TBAI was compounded in a twin-screw mixer at 110° C. The torque of the screws was monitored for 8 minutes.

Example 53 (EX-53)

A mixture of 99.2 parts pre-compounded PLA pellets (PE-1), 0.4 parts J4368, 0.4 parts TBAI was compounded in a twin-screw mixer at 110° C. The torque of the screws was monitored for 8 minutes.

Example 54 (EX-54)

A mixture of 98.8 parts pre-compounded PLA pellets (PE-1), 0.4 parts J4368, 0.8 parts TBAI was compounded in a twin-screw mixer at 110° C. The torque of the screws was monitored for 8 minutes.

Example 55 (EX-55)

A mixture of 98.0 parts pre-compounded PLA pellets (PE-1), 0.4 parts J4368, 1.6 parts TBAI was compounded in a twin-screw mixer at 110° C. The torque of the screws was monitored for 8 minutes.

Example 56 (EX-56)

A mixture of 97.2 parts pre-compounded PLA pellets (PE-1), 0.4 parts J4368, 2.4 parts TBAI was compounded in a twin-screw mixer at 110° C. The torque of the screws was monitored for 8 minutes.

Table 7 summarizes the impact of crosslink catalyst concentration on the reaction between flexible PLA blends and J4368 at 110° C.

TABLE 7

Effect of crosslinking catalyst concentration on the reaction between flexible PLA blends and J4368 at 110° C.

| Sample | Induction time (min) | Reaction time (min) | Maximum torque (Nm) |
|---|---|---|---|
| C-9 | no reaction in 15 min | | 7.4 |
| C-10 | no reaction in 15 min | | 7.4 |
| EX-51 | 3.5 | >7 | n.d. |
| EX-52 | 1 | 5 | 16.0 |
| EX-53 | 1 | 4 | 15.9 |
| EX-54 | 0.25 | 2 | 16.0 |
| EX-55 | 0.25 | 2 | 17.1 |
| EX-56 | 0.25 | 2 | 16 |

Example 57 (EX-57)

A 1.0 g sample of polymer prefoam resin (EX-57) composed of 75.5 parts pre-compounded PLA pellets (PE-1), 0.1 parts J4368, 0.2 parts DTMAB, 5 parts AZO, 1 part color, 10 parts talc, 7 parts citroflex A4, 1 part PEG-functionalized silica nanoparticles was foamed in a mold.

TABLE 8

Characterization of the foam of EX-57

| Foam | Cell diameter (mm) | Cell homogeneity | Cell area (mm$^2$) | Cell roundness | Cell density (cell/cm$^2$) |
|---|---|---|---|---|---|
| EX-57 | 0.362 | 3.36 | 0.180 | 1.247 | 265 |

Preparative Example 5 (PE-5)

A solution of starch in water (25% solids) was mixed with a high shear mixer. The polymer solution was spray dried using a Buchi Mini-Probe B-190 (Buchi Corporation, New Castle, Del.) at a flow rate of 10 RPM and an inlet temperature set at 160° C. (outlet temperature measurement of 75-80° C.). The starch particles were collected in the cyclone and used without further purification.

Preparative Example 6 (PE-6)

A solution of PVP in water (25% solids) was mixed with a high shear mixer. The polymer solution was spray dried using a Buchi Mini-Probe B-190 (Buchi Corporation, New Castle, Del.) at a flow rate of 10 RPM and an inlet temperature set at 160° C. (outlet temperature measurement of 75-80° C.). The PVP particles were collected in the cyclone and used without further purification.

Example 58 (EX-58)

A disk of polymer prefoam resin (EX-58) composed of 93.4 parts pre-compounded pellets (PE-1), 0.4 parts J4368, 0.2 parts DTMAB, 5 parts AZO, and 1 part erucamide was foamed in an oven at 210, 230, or 250° C.

Example 59 (EX-59)

A disk of polymer prefoam resin (EX-59) composed of 88.4 parts pre-compounded pellets (PE-1), 0.4 parts J4368, 0.2 parts DTMAB, 5 parts AZO, 5 parts PVP particles (PE-6), and 1 part erucamide was foamed in an oven at 210, 230, or 250° C.

Example 60 (EX-60)

A disk of polymer prefoam resin (EX-60) composed of 88.4 parts pre-compounded pellets (PE-1), 0.4 parts J4368, 0.2 parts DTMAB, 5 parts AZO, 5 parts starch particles (PE-5), and 1 part erucamide was foamed in an oven at 210, 230, or 250° C.

Example 61 (EX-61)

A disk of polymer prefoam resin (EX-61) composed of 88.4 parts pre-compounded pellets (PE-1), 0.4 parts J4368, 0.2 parts DTMAB, 5 parts AZO, 5 parts talc, and 1 part erucamide was foamed in an oven at 210, 230, or 250° C.

Example 62 (EX-62)

A disk of polymer prefoam resin (EX-62) composed of 88.4 parts pre-compounded pellets (PE-1), 0.4 parts J4368, 0.2 parts DTMAB, 5 parts AZO, 5 parts PS beads, and 1 part erucamide was foamed in an oven at 210, 230, or 250° C.

Example 63 (EX-63)

A disk of polymer prefoam resin (EX-63) composed of 88.4 parts pre-compounded pellets (PE-1), 0.4 parts J4368, 0.2 parts DTMAB, 5 parts AZO, 5 parts glass beads, and 1 part erucamide was foamed in an oven at 210, 230, or 250° C.

TABLE 9

Characterization of foams EX-58 to EX-63

| Temperature (° C.) | Time (min) | Sample | Cell diameter (mm) | Cell density (cell/mm$^2$) | Cell homogeneity |
|---|---|---|---|---|---|
| 210° C. | 9 | EX-58 | 2.21 | 0.1 | 0.75 |
| | | EX-59 | 0.387 | 7.3 | 4.24 |
| | | EX-60 | 0.555 | 3.9 | 3.95 |
| | | EX-61 | 0.507 | 7.2 | 6.21 |
| | | EX-62 | 0.722 | 1.4 | 1.72 |
| | | EX-63 | 0.714 | 2.5 | 5.03 |
| 230° C. | 3.5 | EX-58 | 0.326 | 11.2 | 5.21 |
| | | EX-59 | 0.214 | 28.8 | 6.67 |
| | | EX-60 | 0.45 | 7.9 | 7.30 |
| | | EX-61 | 0.377 | 8.5 | 6.02 |
| | | EX-62 | 0.317 | 6.7 | 1.85 |
| | | EX-63 | 0.334 | 7.2 | 5.38 |
| | 5 | EX-58 | 4 | 0.1 | n/a |
| | | EX-59 | 0.286 | 27.7 | 7.35 |
| | | EX-60 | 0.572 | 5.9 | 4.10 |
| | | EX-61 | 0.5 | 5.6 | 4.95 |

TABLE 9-continued

Characterization of foams EX-58 to EX-63

| Temperature (° C.) | Time (min) | Sample | Cell diameter (mm) | Cell density (cell/mm²) | Cell homogeneity |
|---|---|---|---|---|---|
| | | EX-62 | 2 | 0.1 | n/a |
| | | EX-63 | 0.528 | 4.9 | 4.41 |
| 250° C. | 3.5 | EX-58 | | collapsed foam | |
| | | EX-59 | 0.249 | 14.6 | 6.41 |
| | | EX-60 | 0.426 | 5.9 | 3.80 |
| | | EX-61 | 0.356 | 6.7 | 4.57 |
| | | EX-62 | 0.328 | 6.7 | 4.05 |
| | | EX-63 | 0.334 | 8.3 | 4.41 |

Preparative Example 7 (PE-7)

Preparative example 7 (PE-7) was made by melt compounding 33 parts PLA 4060, 7 parts PLA 4032, 35 parts Vinavil K70 PVAc, and 25 parts HALLGREEN R-8040 (HG R8040) (The HallStar Company, Chicago, Ill.) in DSM twin-screw compounder (DSM Research Netherlands, Heerlen, Netherlands), then pressing into a sheet.

Preparative Example 8 (PE-8)

Preparative example 8 (PE-8) was made by melt compounding 33 parts PLA 4060, 7 parts PLA 4032, 35 parts Vinavil K70 PVAc, and 25 parts HALLGREEN R-8010 (HG R8010) (The HallStar Company, Chicago, Ill.) in DSM twin-screw compounder (DSM Research Netherlands, Heerlen, Netherlands), then pressing into a sheet.

Example 64 (EX-64)

A 39.5 mm×22.6 mm×1.1 mm sample of polymer resin (EX-64) composed of 100 parts of PE-7 was foamed in a pressure vessel using a 30 min soak time at 700 PSI (~4.8 MPa) and 70° C. The pressure was released over 10 min.

Example 65 (EX-65)

A 26.9 mm×16.2 mm×1 mm sample of polymer resin (EX-65) composed of 100 parts of PE-7 was foamed in a pressure vessel using a 30 min soak time at 2000 PSI (~13.8 MPa) and 60° C. The pressure was released over 10 min.

Example 66 (EX-66)

A 37 mm×22.7 mm×1 mm sample of polymer resin (EX-66) composed of 100 parts of PE-1 was foamed in a pressure vessel using a 30 min soak time at 700 PSI (~4.8 MPa) and 70° C. The pressure was released over 10 min.

Example 67 (EX-67)

A 39.7 mm×24.1 mm×1 mm sample of polymer resin (EX-67) composed of 100 parts of PE-1 was foamed in a pressure vessel using a 30 min soak time at 2000 PSI (~13.8 MPa) and 60° C. The pressure was released over 10 min.

Example 68 (EX-68)

A 55.4 mm×22.9 mm×1 mm sample of polymer resin (EX-68) composed of 100 parts of PE-8 was foamed in a pressure vessel using a 30 min soak time at 2000 PSI (~13.8 MPa) and 60° C. The pressure was released over 10 min.

TABLE 10

Characterization of foams EX-64 to EX-68

| Sample | Change in volume* $((V_f/V_i) \times 100))$ | Mass change* $(((m_f - m_i)/m_i) \times 100)$ | $Tg_i^*$ (° C.) | $Tg_f^*$ (° C.) |
|---|---|---|---|---|
| EX-64 | 778 | 0.2 | 18.1 | 17.8 |
| EX-65 | 343 | −2.5 | 18.1 | 22.0 |
| EX-66 | 191 | 0.1 | 7.8 | 5.3 |
| EX-67 | 161 | −18.8 | 7.8 | 41.4 |
| EX-68 | 425 | −0.4 | 23.2 | 27.2 |

*$V_f$ = volume of foamed foamed; $V_i$ = volume of unfoamed sample; $m_f$ = mass of foamed sample; $m_i$ = mass of unfoamed sample; $Tg_i$ = glass transition temperature of unfoamed sample; $Tg_f$ = glass transition temperature of foamed sample.

What is claimed:

1. A foam composition comprising:
   a polylactic acid polymer in an amount of at least 10 weight percent and no greater than 90 weight percent, based on the total weight of the foam composition;
   a second polymer having a $T_g$ of at least 25° C. in an amount of at least 20 weight percent and no greater than 50 weight percent, based on the total weight of the foam composition, wherein the second polymer is polyvinyl acetate; and
   a plasticizer in an amount of 5 weight percent to 50 weight percent, based on the total weight of the foam composition;
   wherein the foam composition comprises a closed cell foam and wherein the foam composition has a $T_g$ of less than 25° C.

2. The foam composition of claim 1, wherein the polylactic acid polymer comprises an amorphous polylactic acid polymer.

3. The foam composition of claim 1, wherein the polylactic acid polymer comprises a semicrystalline polylactic acid polymer.

4. The foam composition of claim 1, further comprising at least one nucleating agent selected from a cell nucleating agent, a crystallization nucleating agent, a cell stabilizer, and a combination thereof.

5. The foam composition of claim 4, wherein the cell stabilizer comprises silica nanoparticles functionalized with a polyethylene glycol silane.

6. The foam composition of claim 1, further comprising a crosslinking agent.

7. The foam composition of claim 1, further comprising a crosslink catalyst comprising an alkyl or alkenyl ammonium, phosphonium, or imidizolium salt.

8. The foam composition of claim 7, wherein the crosslink catalyst is of formula (I), (II), (III), or (IV):

$Q(R^1)_4 X$      (I);

$QR^1(R^2)_3 X$      (II);

$QR^3(R^2)_3 X$      (II);

$Q(R^3)_3 R^1 X$      (IV);

wherein Q is nitrogen or phosphorous; $R^1$ is a $C_1$-$C_{20}$ alkyl or alkenyl group; $R^2$ is a $C_1$-$C_8$ alkyl or alkenyl group; $R^3$ is a phenyl group, a benzyl group, or a polycyclic aromatic hydrocarbon group; and X is an anion selected from bromide, iodide, chloride, acetate, sulfate, carbonate, phosphate, tosylate, or hexafluorophosphase.

9. The foam composition of claim 1, wherein the composition does not exhibit plasticizer migration when aged at 80° C. for 24 hours.

10. The foam composition of claim 1, wherein the foam composition comprises a rough surface morphology.

11. A foam composition comprising:
a polylactic acid polymer in an amount of at least 20 weight percent and no greater than 90 weight percent, based on the total weight of the foam composition;
a second polymer having a $T_g$ of at least 25° C. in an amount of at least 20 weight percent and no greater than 50 weight percent, based on the total weight of the foam composition, wherein the second polymer is polyvinyl acetate; and
a plasticizer in an amount of 5 weight percent to 50 weight percent, based on the total weight of the foam composition;
wherein the foam composition comprises an open celled foam and wherein the foam composition has a $T_g$ of less than 25° C.

* * * * *

UNITED STATES PATENT AND TRADEMARK OFFICE
CERTIFICATE OF CORRECTION

PATENT NO. : 11,407,872 B2
APPLICATION NO. : 16/308642
DATED : August 9, 2022
INVENTOR(S) : Joshua Michael Fishman et al.

It is certified that error appears in the above-identified patent and that said Letters Patent is hereby corrected as shown below:

In the Claims

<u>Column 36</u>
Line 53 (approx.), In Claim 8, delete "$QR^3(R^2)_3X$ (II);" and insert -- $QR^3(R^2)_3X$ (III); --, therefor.

Signed and Sealed this
Ninth Day of May, 2023

Katherine Kelly Vidal
*Director of the United States Patent and Trademark Office*